US006756228B2

(12) United States Patent
Tall et al.

(10) Patent No.: US 6,756,228 B2
(45) Date of Patent: Jun. 29, 2004

(54) ATHEROSCLEROSIS SUSCEPTIBILITY GENE LOCUS 1 (ATHSQ1) AND ATHEROSCLEROSIS SUSCEPTIBILITY GENE LOCUS 2 (ATHSQ2)

(75) Inventors: Alan R. Tall, Cresskill, NJ (US); Carrie L. Welch, Sleepy Hollow, NY (US); Chien-Ping Liang, Richardson, TX (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 09/898,554

(22) Filed: Jul. 2, 2001

(65) Prior Publication Data

US 2003/0068673 A1 Apr. 10, 2003

(51) Int. Cl.[7] .......................... C12N 15/85; C12N 1/21; C12N 1/15; C12N 15/63; C07H 21/04
(52) U.S. Cl. ............... 435/325; 435/252.3; 435/254.11; 435/254.2; 435/320.1; 536/23.5; 530/350
(58) Field of Search .............................. 535/23.1, 23.5, 535/24.3; 435/320.1, 325, 252.3, 254.11, 419, 254.2; 530/350

(56) References Cited

U.S. PATENT DOCUMENTS

| 5,750,367 A | 5/1998 | Chan et al. |
| 5,962,260 A | 10/1999 | Sawamura et al. |
| 6,197,937 B1 | 3/2001 | Sawamura et al. |

OTHER PUBLICATIONS

Park et al, GenBank, Accession No. AF303744, Jan. 2, 2001.*
Park et al, SPTREMBL, Accession No. Q9EQ09, Mar. 1, 2001.*
Mehta et al., Identification, Regulation, and Function of a Novel Lectin–like Oxidized Low–Density Lipoprotein Receptor. Journal of the American College of Cardiology. May 2002, vol. 39, No. 9, pp. 1429–1435.
Li et al., Statins Modulate Oxidized Low–Density Lipoprotein–Mediated Adhesion Molecule Expression in Human Coronary Artery Enthothelial Cells: Role of LOX–1. Aug. 2002, vol. 302, No. 2, pp. 601–605.
White, et al., Identification of Peptides that Target the Endothelial Cell–Specific LOX–1 Receptor. Hypertension. Feb. 2001, vol. 37, No. 2, pp. 449–455.
Yamada, et al., Scavenger Receptor Family Proteins: Roles for Atherosclerosis, Host Defense, and Diorders of the Central Nervous System. Jul. 1998, vol. 54, No. 7, pp. 628–640.
Cominacini, L. et al. Oxidized low density lipoprotein (ox–LDL) binding to ox–LDL receptor–1 in endothelial cells induces the activation of NF–κB through an increased production of intracellular reactive oxygen species. *Journal of Biological Chemistry* 275(17): 12633–12638 (Apr. 28, 2000).

Cominacini, L. et al. The binding of oxidized low–density lipoprotein (ox–LDL) to ox–LDL receptor–1 reduces the intracellular concentration of nitric oxide in endothelial cells through an increased production of superoxide. *J. Biol. Chem.* 276 (17):13750–5 (Apr. 27, 2001); published as Manuscript M010612200 on Jan. 24, 2001.
Draude, G., Hrboticky, N. and Lorenz, R.L. (1999) The expression of the lectin–like oxidized low–density lipoprotein receptor (LOX–1) on human vascular smooth muscle cells and monocytes and its down–regulation by lovastatin. *Biochemical Pharmacology* 57:383–386.
Draude, G. and Lorenz, R.L., (2000) "TGF–β1 downregulates CD36 and scavenger receptor A but upregulates LOX–1 in human macrophages." *Am. J. Physiol. Heart Circ. Physiol.* 278: H1042–H1048.
Hoshikawa, H. et al., (1998) High affinity binding of oxidized LDL to mouse lectin–like oxidized LDL receptor (LOX–1). Biochemical and Biophysical Research Communications 245: 841–846.
Kakutani, M., et al. (2000) A platelet–endothelium interaction mediated by lectin–like oxidized low–density lipoprotein receptor–1. *Proceedings of the National Academy of Sciences* 97: 360–364 (Jan. 4, 2000).
Kataoka, H. et al. Biosythesis post–translational processing of lectin–like oxidized low density lipoprotein receptor–1 (LOX–1). *J. Biol. Chem.* 275(9):6573–6579 (Mar. 3, 2000).
Kume, N. and Kita, T. (2001) Lectin–like oxidized low–density lipoprotein receptor–1 (LOX–1) in atherogenesis. *Trends Cardiovasc. Med.* 11:22–25.
Li, D. and Mehta, J. L. (2000) Antisense to LOX–1 inhibits oxidized LDL–mediated upregulation of monocyte chemoattractant protein–1 and monocyte adhesion to human coronary artery endothelial cells. *Circulation* 101:2889–2895.
Li, D., et al. (2000) Oxidized LDL upregulates angiotensinII type 1 receptor expression in cultured human coronary artery endothelial cells. The potential role of transcription factor NF–κB, *Circulation* 102:1970–1976.
Li, D. et al. (2000) Upregulation of endothelial receptor for oxidized LDL (LOX–1) by oxidized LDL and implications in apoptosis of human coronary artery endothelial cells. Evidence from use of antisense LOX–1 mRNA and chemical inhibitors. *Anterioscler. Thromb. Vacs. Biol.* 20:1116–1122.

(List continued on next page.)

Primary Examiner—Yvonne Eyler
Assistant Examiner—Ruixiang Li
(74) Attorney, Agent, or Firm—John P. White; Cooper & Dunham LLP

(57) ABSTRACT

This invention provides isolated nucleic acids encoding mammalian membrane-bound and soluble LOX-1 receptors. The invention also provides methods of identifying agents that inhibit the activity of a mammalian LOX-1 receptor. This invention further provides methods of preventing or treating atherosclerosis, heart disease or stroke in a subject which comprise reducing the activity of membrane-bound LOX-1 receptor.

9 Claims, 17 Drawing Sheets

OTHER PUBLICATIONS

Li, X. et al. (1998) Assignment of the human oxidized low-density lipoprotein receptor gene (OLRI) to chromosome 12p13.1→p12.3, and identification of a polymorphic CA-repeat marker in the OLRI gene, *Cytogenet Cell Genet* 86: 34–36.

Minami, M. et al. (2000) Transforming Growth Factor-$\beta_1$ increases the expression of lectin-like oxidized low-density lipoprotein receptor-1, *Biochemical and Biophysical Research Communications* 272:357–361.

Morikawa, H. et al. (1998) Expression of lectin-like oxidized low density lipoprotein receptor-1 in human and murine macrophages: upregulated exression by TNF-$\alpha$, *Federation of European Biochemical Societies* 440: 29–32.

Murase, T. et al. (2000) Identification of soluble forms of lectin-like oxidized LDL receptor-1. *Anterioscler Thromb Vasc. Biol.* 20: 715–720.

Nagase, M. et al., (1998) Genomic organization and regulation of expression of the lectin-like oxidized low-density lipoprotein receptor (LOX-1) gene. The Journal of Biological Chemistry 273 (50): 33702–33707.

Nagase, M. et al. (1998) Unique repetitive sequence and unexpected regulation of expression of rat endothelial receptor for oxidized low-density lipoprotein (LOX-1). *Biochem. J.* 330: 1417–1422.

Nagase, M. et al. (2000) Expression of LOX-1, an oxidized low-density lipoprotein receptor, in experimental hypertensive glomerulosclerisis, *J. Am. Soc. Nephrol.* 11:1826–1836.

Renedo, M. et al. (2000) A sequence-ready physical map of the region containing the human natural killer gene complex on chromosome 12p12.3–p13.2. *Genomics* 65: 129–136.

Sawamura, T. et al. (1997) An endothelial receptor for oxidized low-density liporotein. *Nature* 386: 73–77.

Yamanaka, S., et al. (1998) The human gene encoding the lectin-type oxidized LDL receptor (OLR1) is a novel member of the natural killer gene complex with a unique expression profile. *Genomics* 54: 191–199.

Li, X., Bouzyk, M.M., and Wang, X.K. (1998) Human oxidized low density lipoprotein receptor: characterization of the full length cDNA sequence and assignment to human chromosome 12p13.1–12.3. GenBank Accession No. AF035776, published Dec. 2, 1998.

* cited by examiner

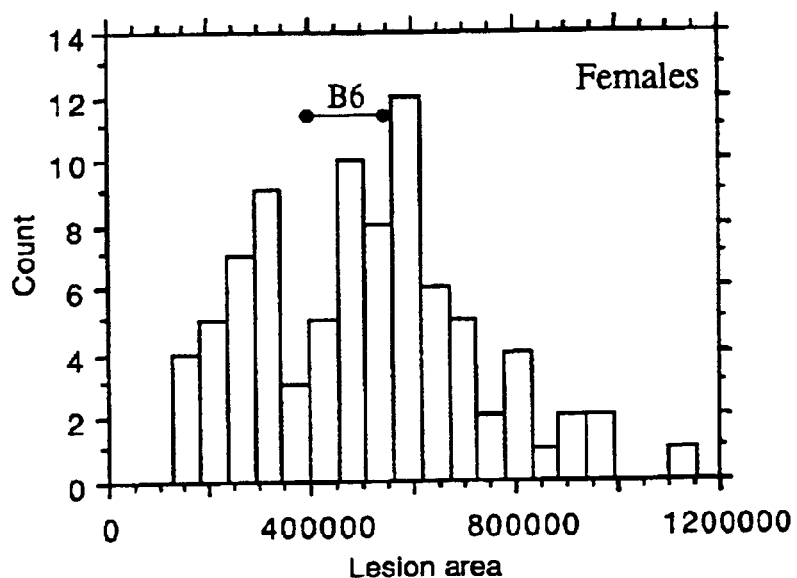
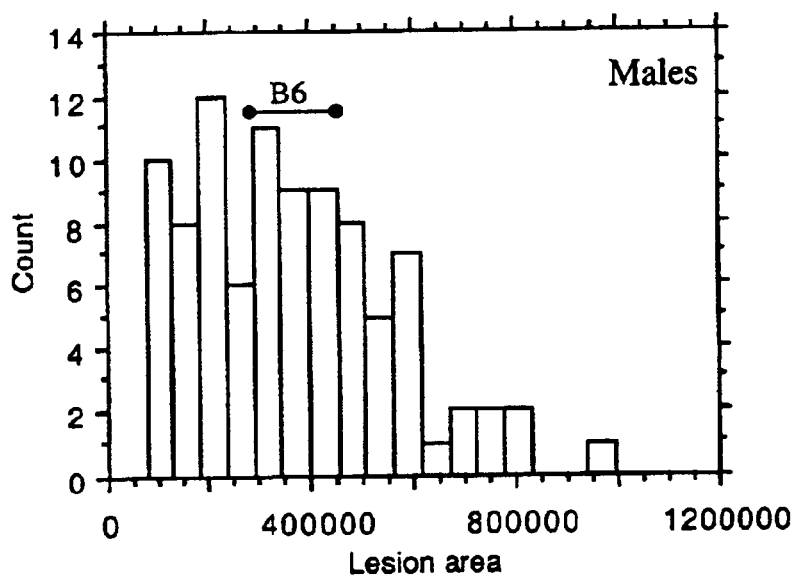
Figure 1

```
B-Isoform 1    1  ATGACTTTTG ATGACAAGAT GAAGCCTGCG AATGACGAGC CTGATCAGAA
M-Isoform 1    1  ATGACTTTTG ATGACAAGAT GAAGCCTGCG AATGACGAGC CTGATCAGAA
Isoform 7      1  ATGACTTTTG ATGACAAGAT GAAGCCTGCG AATGACGAGC CTGATCAGAA
Isoform 8      1  ATGACTTTTG ATGACAAGAT GAAGCCTGCG AATGACGAGC CTGATCAGAA
Isoform 9      1  ATGACTTTTG ATGACAAGAT GAAGCCTGCG AATGACGAGC CTGATCAGAA B-Isoform 1   51  GTCATGTGGC AAGAAGCCTA AAGGTCTGCA TTTGCTTTCT TCCCCATGGT
M-Isoform 1   51  GTCATGTGGC AAGAAGCCTA AAGGTCTGCA TTTGCTTTCT TCCCCATGGT
Isoform 7     51  GTCATGTGGC AAGAAGCCTA AAG------- ---------- ----------
Isoform 8     51  GTCATGTGGC AAGAAGCCTA AAG------- ---------- ----------
Isoform 9     51  GTCATGTGGC AAGAAGCCTA AAG------- ---------- ----------
                                                                       |<-

B-Isoform 1  101  GGTTCCCTGC TGCTATGACT CTGGTCATCC TCTGCCTGGT GTTGTCAGTG
M-Isoform 1  101  GGTTCCCTGC TGCTATGACT CTGGTCATCC TCTGCCTGGT GTTGTCAGTG
Isoform 7     73  ---------- ---------- ---------- ---------- ----------
Isoform 8     73  ---------- ---------- ---------- ---------- ----------
Isoform 9     73  ---------- ---------- ---------- ---------- ----------
                     <---             TM B-Isoform 1  151  ACCCTTATTG TACAGTGGAC ACAATTACGC CAGGTATCTG ACCTCTTAAA
M-Isoform 1  151  ACCCTTATTG TACAGTGGAC ACAATTACGC CAGGTATCTG ACCTCTTAAA
Isoform 7     73  ---------- ---------- ---------- ---------- ----------
Isoform 8     73  ---------- ---------- ---------- ---------- ----------
Isoform 9     73  ---------- ---------- ---------- ---------- ----------
                        TM              --->|

B-Isoform 1  201  ACAATACCAA GCGAACCTTA CTCAGCAGGA TCGTATCCTG GAAGGGCAGA
M-Isoform 1  201  ACAATACCAA GCGAACCTTA CTCAGCAGGA TCGTATCCTG GAAGGGCAGA
Isoform 7     73  ---------- ---------- ---------- ---------- ----------
Isoform 8     73  ---------- ---------- ---------- ---------- ----------
Isoform 9     73  ---------- ---------- ---------- ---------- ----------

B-Isoform 1  251  TGTTAGCCCA GCAGAAGGCA GAAAACACTT CACAGGAATC AAAGAAGGAA
M-Isoform 1  251  TGTTAGCCCA GCAGAAGGCA GAAAACACTT CACAGGAATC AAAGAAGGAA
Isoform 7     73  ---------- ---------- ---------- ---------- ----------
Isoform 8     73  ---------- ---------- ---------- ---------- ----------
Isoform 9     73  ---------- ---------- ---------- ---------- ----------
                                                              |<--- 1st repeat B-Isoform 1  301  CTGAAAGGAA AGATAGACAC CCTCACCCAG AAGCTGAACG AGAAATCCAA
M-Isoform 1  301  CTGAAAGGAA AGATAGACAC CCTCACCCAG AAGCTGAACG AGAAATCCAA
Isoform 7     73  ---------- ---------- ---------- ---------- ----------
Isoform 8     73  ---------- ---------- ---------- ---------- ----------
Isoform 9     73  ---------- ---------- ---------- ---------- ----------
                                       1st repeat
```

Figure 3A

```
B-Isoform 1 351   AGAGCAGGAG GAGCTTCTAC AGAAGAATCA GAACCTCCAA GAAGCCCTGC
M-Isoform 1 351   AGAGCAGGAG GAGCTTCTAC AGAAGAATCA GAACCTCCAA GAAGCCCTGC
Isoform 7    73   ---------- ---------- ---------- ---------- ----------
Isoform 8    73   ---------- ---------- ---------- ---------- ----------
Isoform 9    73   ---------- ---------- ---------- ---------- ----------
                                         1st repeat B-Isoform 1 401   AAAGAGCTGC AAACTCTTCA GAGGAGTCCC AGAGAGAACT CAAGGGAAAG
M-Isoform 1 401   AAAGAGCTGC AAACTCTTCA GAGGAGTCCC AGAGAGAACT CAAGGGAAAG
Isoform 7    73   ---------- ---------- -AGGAGTCCC AGAGAGAACT CAAGGGAAAG
Isoform 8    73   ---------- ---------- ---------- ---------- ----------
Isoform 9    73   ---------- ---------- ---------- ---------- ----------
                     1st repeat   --->|<---

B-Isoform 1 451   ATAGACACCA TCACCCGGAA GCTGGACGAG AAATCCAAAG AGCAGGAGGA
M-Isoform 1 451   ATAGACACCA TCACCCGGAA GCTGGACGAG AAATCCAAAG AGCAGGAGGA
Isoform 7   102   ATAGACACCA TCACCCGGAA GCTGGACGAG AAATCCAAAG AGCAGGAGGA
Isoform 8    73   ---------- ---------- ---------- ---------- ----------
Isoform 9    73   ---------- ---------- ---------- ---------- ----------
                                         2nd repeat B-Isoform 1 501   GCTTCTGCAG ATGATTCAGA ACCTCCAAGA AGCCCTGCAG AGAGCTGCAA
M-Isoform 1 501   GCTTCTGCAG ATGATTCAGA ACCTCCAAGA AGCCCTGCAG AGAGCTGCAA
Isoform 7   152   GCTTCTGCAG ATGATTCAGA ACCTCCAAGA AGCCCTGCAG AGAGCTGCAA
Isoform 8    73   ---------- ---------- ---------- ---------- ----------
Isoform 9    73   ---------- ---------- ---------- ---------- ----------
                                         2nd repeat B-Isoform 1 551   ACTCTTCAGA GGAGTCCCAG AGAGAACTCA AGGGAAAGAT AGACACCCTC
M-Isoform 1 551   ACTCTTCAGA GGAGTCCCAG AGAGAACTCA AGGGAAAGAT AGACACCCTC
Isoform 7   202   ACTCTTCAGA GGAGTCCCAG AGAGAACTCA AGGGAAAGAT AGACACCCTC
Isoform 8    73   ---------A GGAGTCCCAG AGAGAACTCA AGGGAAAGAT AGACACCCTC
Isoform 9    73   ---------- ---------- ---------- ---------- ----------
                     2nd ---->|<----    3rd repeat B-Isoform 1 601   ACCTTGAAGC TGAACGAGAA ATCCAAAGAG CAGGAGGAGC TTCTACAGAA
M-Isoform 1 601   ACCTTGAAGC TGAACGAGAA ATCCAAAGAG CAGGAGGAGC TTCTACAGAA
Isoform 7   252   ACCTTGAAGC TGAACGAGAA ATCCAAAGAG CAGGAGGAGC TTCTACAGAA
Isoform 8   114   ACCTTGAAGC TGAACGAGAA ATCCAAAGAG CAGGAGGAGC TTCTACAGAA
Isoform 9    73   ---------- ---------- ---------- ---------- ----------
                                         3rd repeat B-Isoform 1 651   GAATCAGAAC CTCCAAGAAG CCCTGCAAAG AGCTGCAAAC TTTTCAGGTC
M-Isoform 1 651   GAATCAGAAC CTCCAAGAAG CCCTGCAAAG AGCTGCAAAC TTTTCAGGTC
Isoform 7   302   GAATCAGAAC CTCCAAGAAG CCCTGCAAAG AGCTGCAAAC TTTTCAGGTC
Isoform 8   164   GAATCAGAAC CTCCAAGAAG CCCTGCAAAG AGCTGCAAAC TTTTCAGGTC
Isoform 9    73   ---------- ---------- ---------- ---------- -------GTC
                        3rd repeat                              ---->|
```

Figure 3B

```
B-Isoform 1  701   CTTGTCCACA AGACTGGCTC TGGCATAAAG AAAACTGTTA CCTCTTCCAT
M-Isoform 1  701   CTTGTCCACA AGACTGGCTC TGGCATAAAG AAAACTGTTA CCTCTTCCAT
Isoform 7    352   CTTGTCCACA AGACTGGCTC TGGCATAAAG AAAACTGTTA CCTCTTCCAT
Isoform 8    214   CTTGTCCACA AGACTGGCTT TGGCATAAAG AAAACTGTTA CCTCTTCCAT
Isoform 9     75   CTTGTCCACA AGACTGGCTC TGGCATAAAG AAAACTGTTA CCTCTTCCAT B-Isoform 1  751   GGGCCCCTTA GCTGGGAAAA AAACCGGCAG ACCTGCCAAT CTTTGGGTGG
M-Isoform 1  751   GGGCCCTTTA GCTGGGAAAA AAACCGGCAG ACCTGCCAAT CTTTGGGTGG
Isoform 7    402   GGGCCCTTTG GCTGGGAAAA AAACCGGCAG ACCTGCCAAT CTTTGGGTGG
Isoform 8    264   GGGCCCTTTA GCTGGGAAAA AAACCGGCAG ACCTGCCAAT CTTTGGGTGG
Isoform 9    125   GGGCCCTTTA GCTGGGAAAA AAACCGGCAG ACCTGCCAAT CTTTGGGTGG B-Isoform 1  801   CCAGTTACTA CAAATTAATG GTGCAGATGA TCTGACATTC ATCTTACAAG
M-Isoform 1  801   CCAGTTACTA CAAATTAATG GTGCAGATGA TCTGACATTC ATCTTACAAG
Isoform 7    452   CCAGTTACTA CAAATTAATG GTGCAGATGA TCTGACATTC ATCTTACAAG
Isoform 8    314   CCAGTTACTA CAAATTAATG GTGCAGATGA TCTGACATTC ATCTTACAAG
Isoform 9    175   CCAGTTACTA CAAATTAATG GTGCAGATGA TCTGACATTC ATCTTACAAG B-Isoform 1  851   CAATTTCCCA TACCACCTCC CCGTTCTGGA TTGGATTGCA TCGGAAGAAG
M-Isoform 1  851   CAATTTCCCA TACCACCTCC CCATTCTGGA TTGGATTGCA TCGGAAGAAG
Isoform 7    502   CAATTTCCCA TACCACCTCC CCATTCTGGA TTGGATTGCA TCGGAAGAAG
Isoform 8    364   CAATTTCCCA TACCACCTCC CCATTCTGGA TTGGATTGCA TCGGAAGAAG
Isoform 9    225   CAATTTCCCA TACCACCTCC CCATTCTGGA TTGGATTGCA TCGGAAGAAG B-Isoform 1  901   CCTGGCCAAC CATGGCTATG GGAGAATGGA ACTCCTTTGA ATTTTCAATT
M-Isoform 1  901   CCTGGCCAAC CATGGCTATG GGAGAATGGA ACTCCTTTGA ATTTTCAATT
Isoform 7    552   CCTGGCCAAC CATGGCTATG GGAGAATGGA ACTCCTTTGA ATTTTCAATT
Isoform 8    414   CCTGGCCAAC CATGGCTATG GGAGAATGGA ACTCCTTTGA ATTTTCAATT
Isoform 9    275   CCTGGCCAAC CATGGCTATG GGAGAATGGA ACTCCTTTGA ATTTTCAATT B-Isoform 1  951   CTTTAAGACC AGGGGCGTTT CTTTACAGCT ATATTCATCA GGCAACTGTG
M-Isoform 1  951   CTTTAAGACC AGGGGCGTTT CTTTACAGCT ATATTCATCA GGCAACTGTC
Isoform 7    602   CTTTAAGACC AGGGGCGTTT CTTTACAGCT ATATTCATCA AGCAACTGTG
Isoform 8    464   CTTTAAGACC AGGGGCGTTT CTTTACAGCT ATATTCATCA GGCAACTGTG
Isoform 9    325   CTTTAAGACC AGGGGCGTTT CTTTACAGCT ATATTCATCA GGCAACTGTG B-Isoform1  1001   CATACCTTCA AGACGGAGCT GTGTTCGCTG AAAACTGCAT TCTAATTGCA
M-Isoform1  1001   CATACCTTCA AGACGGAGCT GTGTTCGCTG AAAACTGCAT TCTAATTGCA
Isoform 7    652   CATACCTTCA AGACGGAGCT GTGTTCGCTG AAAACTGCAT TCTAATTGCA
Isoform 8    514   CATACCTTCA AGACGGAGCT GTGTTCGCTG AAAACTGCAT TCTAATTGCA
Isoform 9    375   CATACCTTCA AGACGGAGCT GTGTTCGCTG AAAACTGCAT TCTAATTGCA B-Isoform1  1051   TTCAGCATAT GTCAGAAGAA GACAAATCAT TTGCAAATTT AG--------
M-Isoform1  1051   TTCAGCATAT GTCAGAAGAA GACAAATCAT TTGCAAATTT AG--------
Isoform 7    702   TTCAGCATAT GTCAGAAGAA GACAAATCAT TTGCAAATTT AG--------
Isoform 8    564   TTCAGCATAT GTCAGAAGAA GACAAATCAT TTGCAAATTT AG--------
Isoform 9    425   TTCAGCATAT GTCAGAAGAA GACAAATCAT TTGCAAATTT AG--------
```

Figure 3C

```
Isoform 1
atg act ttt gat gac aag atg aag cct gcg aat gac gag cct gat cag        48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca        96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg        144
Trp Trp Phe Pro Ala Ala Met Thr Leu Val Ile Leu Cys Leu Val Leu
        35                  40                  45 tca gtg acc ctt att gta cag tgg aca caa tta cgc cag gta tct gac        192
Ser Val Thr Leu Ile Val Gln Trp Thr Gln Leu Arg Gln Val Ser Asp
    50                  55                  60 ctc tta aaa caa tac caa gcg aac ctt act cag cag gat cgt atc ctg        240
Leu Leu Lys Gln Tyr Gln Ala Asn Leu Thr Gln Gln Asp Arg Ile Leu
65              70                  75                  80 gaa ggg cag atg tta gcc cag cag aag gca gaa aac act tca cag gaa        288
Glu Gly Gln Met Leu Ala Gln Gln Lys Ala Glu Asn Thr Ser Gln Glu
            85                  90                  95 tca aag aag gaa ctg aaa gga aag ata gac acc ctc acc cag aag ctg        336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac        384
Asn Glu Lys Ser Lys Glu Gln Glu Glu Leu Leu Gln Lys Asn Gln Asn
        115                 120                 125 ctc caa gaa gcc ctg caa aga gct gca aac tct tca gag gag tcc cag        432
Leu Gln Glu Ala Leu Gln Arg Ala Ala Asn Ser Ser Glu Glu Ser Gln
    130                 135                 140 aga gaa ctc aag gga aag ata gac acc atc acc cgg aag ctg gac gag        480
Arg Glu Leu Lys Gly Lys Ile Asp Thr Ile Thr Arg Lys Leu Asp Glu
145             150                 155                 160 aaa tcc aaa gag cag gag gag ctt ctg cag atg att cag aac ctc caa        528
Lys Ser Lys Glu Gln Glu Glu Leu Leu Gln Met Ile Gln Asn Leu Gln
            165                 170                 175 gaa gcc ctg cag aga gct gca aac tct tca gag gag tcc cag aga gaa        576
Glu Ala Leu Gln Arg Ala Ala Asn Ser Ser Glu Glu Ser Gln Arg Glu
            180                 185                 190 ctc aag gga aag ata gac acc ctc acc ttg aag ctg aac gag aaa tcc        624
Leu Lys Gly Lys Ile Asp Thr Leu Thr Leu Lys Leu Asn Glu Lys Ser
        195                 200                 205 aaa gag cag gag gag ctt cta cag aag aat cag aac ctc caa gaa gcc        672
Lys Glu Gln Glu Glu Leu Leu Gln Lys Asn Gln Asn Leu Gln Glu Ala
    210                 215                 220
```

Figure 4A

```
Isoform 1
ctg caa aga gct gca aac ttt tca ggt cct tgt cca caa gac tgg ctc      720
Leu Gln Arg Ala Ala Asn Phe Ser Gly Pro Cys Pro Gln Asp Trp Leu
225             230                 235                 240 tgg cat aaa gaa aac tgt tac ctc ttc cat ggg cct ttt agc tgg gaa      768
Trp His Lys Glu Asn Cys Tyr Leu Phe His Gly Pro Phe Ser Trp Glu
                245                 250                 255 aaa aac cgg cag acc tgc caa tct ttg ggt ggc cag tta cta caa att      816
Lys Asn Arg Gln Thr Cys Gln Ser Leu Gly Gly Gln Leu Leu Gln Ile
            260                 265                 270 aat ggt gca gat gat ctg aca ttc atc tta caa gca att tcc cat acc      864
Asn Gly Ala Asp Asp Leu Thr Phe Ile Leu Gln Ala Ile Ser His Thr
        275                 280                 285 acc tcc cca ttc tgg att gga ttg cat cgg aag aag cct ggc caa cca      912
Thr Ser Pro Phe Trp Ile Gly Leu His Arg Lys Lys Pro Gly Gln Pro
    290                 295                 300 tgg cta tgg gag aat gga act cct ttg aat ttt caa ttc ttt aag acc      960
Trp Leu Trp Glu Asn Gly Thr Pro Leu Asn Phe Gln Phe Phe Lys Thr
305                 310                 315                 320 agg ggc gtt tct tta cag cta tat tca tca ggc aac tgt gca tac ctt     1008
Arg Gly Val Ser Leu Gln Leu Tyr Ser Ser Gly Asn Cys Ala Tyr Leu
            325                 330                 335 caa gac gga gct gtg ttc gct gaa aac tgc att cta att gca ttc agc     1056
Gln Asp Gly Ala Val Phe Ala Glu Asn Cys Ile Leu Ile Ala Phe Ser
        340                 345                 350 ata tgt cag aag aag aca aat cat ttg caa att tag                     1092
Ile Cys Gln Lys Lys Thr Asn His Leu Gln Ile
    355                 360
```

Figure 4B

Isoform 2

```
atg act ttt gat gac aag atg aag cct gcg aat gac gag cct gat cag        48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca         96
Lys Ser Cys Gly Lys Lys Pro Lys Gly Leu His Leu Leu Ser Ser Pro
                20              25                  30 tgg tgg ttc cct gct gct atg act ctg gtc atc ctc tgc ctg gtg ttg        144
Trp Trp Phe Pro Ala Ala Met Thr Leu Val Ile Leu Cys Leu Val Leu
        35              40                  45 tca gtg acc ctt att gta cag tgg aca caa tgatcgtatc ctggaagggc          194
Ser Val Thr Leu Ile Val Gln Trp Thr Gln
    50              55
```
agatgttagc ccagcagaag gcagaaaaca cttcacagga atcaaagaag gaactgaaag     254
gaaagataga caccctcacc cagaagctga acgagaaatc caaagagcag gaggagcttc     314
tacagaagaa tcagaacctc caagaagccc tgcaaagagc tgcaaactct tcagaggagt     374
cccagagaga actcaaggga aagatagaca ccatcacccg gaagctggac gagaaatcca     434
aagagcagga ggagcttctg cagatgattc agaacctcca agaagccctg cagagagctg     494
caaactcttc agaggagtcc cagagagaac tcaagggaaa gatagacacc ctcaccttga     554 gctgaacga gaaatccaaa gagcaggagg agcttctaca gaagaatcag aacctccaag     614
aagccctgca aagagctgca aacttttcag gtccttgtcc acaagactgg ctctggcata     674
aagaaaactg ttacctcttc cgtgggccct ttactgggaa aaaagccggc agacctgcca     734 atcttgggt ggcagttact acaaattaat gggcagatg                            773

Figure 5

```
Isoform 3
atg act ttt gat gac aag atg aag cct gcg aat gac gag cct gat cag      48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca      96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg     144
Trp Trp Phe Pro Ala Ala Met Thr Leu Val Ile Leu Cys Leu Val Leu
        35                  40                  45 tca gtg acc ctt att gta cag tgg aca caa tta cgc cag gta tct gac     192
Ser Val Thr Leu Ile Val Gln Trp Thr Gln Leu Arg Gln Val Ser Asp
50                  55                  60 ctc tta aaa caa tac caa gcg aac ctt act cag cag gat cgt atc ctg     240
Leu Leu Lys Gln Tyr Gln Ala Asn Leu Thr Gln Gln Asp Arg Ile Leu
65                  70                  75                  80 gaa ggg cag atg tta gcc cag cag aag gca gaa aac act tca ccg caa     288
Glu Gly Gln Met Leu Ala Gln Gln Lys Ala Glu Asn Thr Ser Pro Gln
                85                  90                  95 tca aag aag gaa ctg aaa gga aag ata gac acc ctc acc cag aag ctg     336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac     384
Asn Glu Lys Ser Lys Glu Gln Glu Glu Leu Leu Gln Lys Asn Gln Asn
        115                 120                 125 ctc caa gaa gcc ctg caa aga gct gca aac tct tca gag gag tcc cag     432
Leu Gln Glu Ala Leu Gln Arg Ala Ala Asn Ser Ser Glu Glu Ser Gln
    130                 135                 140 aga gaa ctc aag gga aag ata gac acc ctc acc ttg aag ctg aac gag     480
Arg Glu Leu Lys Gly Lys Ile Asp Thr Leu Thr Leu Lys Leu Asn Glu
145                 150                 155                 160 aaa tcc aaa gag cag                                                  495
Lys Ser Lys Glu Gln
                165
```

Figure 6

```
Isoform 4
atg act ttt gat gac aag atg aag cct gcg aat gac gag cct gat cag        48
Met Thr Phe Asp Asp Lys Met Lys Pro Ala Asn Asp Glu Pro Asp Gln
 1               5                  10                  15 aag tca tgt ggc aag aag cct aaa ggt ctg cat ttg ctt tct tcc cca        96
Lys Ser Cys Gly Lys Lys Pro Lys Gly Leu His Leu Leu Ser Ser Pro
                20                  25                  30 tgg tgg ttc cct gct gct atg act ctg gtc atc ctc tgc ctg gtg ttg       144
Trp Trp Phe Pro Ala Ala Met Thr Leu Val Ile Leu Cys Leu Val Leu
            35                  40                  45 tca gtg acc ctt att gta cag tgg aca caa tta cgc cag gta tct gac       192
Ser Val Thr Leu Ile Val Gln Trp Thr Gln Leu Arg Gln Val Ser Asp
        50                  55                  60 ctc tta aaa caa tac caa gcg aac ctt act cag cag gat cgt atc ctg       240
Leu Leu Lys Gln Tyr Gln Ala Asn Leu Thr Gln Gln Asp Arg Ile Leu
 65                  70                  75                  80 gaa ggg cag atg tta gcc cag cag aag gca gaa aac act tca cag gaa       288
Glu Gly Gln Met Leu Ala Gln Gln Lys Ala Glu Asn Thr Ser Gln Glu
                 85                  90                  95 tca aag aag gaa ctg aaa gga aag ata gac acc ctc acc cag aag ctg       336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac       384
Asn Glu Lys Ser Lys Glu Gln Glu Glu Leu Leu Gln Lys Asn Gln Asn
        115                 120                 125 ctc caa gaa gcc ctg caa aga gct gca aac ttt tca ggt cct tgt cca       432
Leu Gln Glu Ala Leu Gln Arg Ala Ala Asn Phe Ser Gly Pro Cys Pro
130                 135                 140 caa gac tgg ctc tgg cat aaa gaa aac tgt tac ctc ttc cat ggg ccc       480
Gln Asp Trp Leu Trp His Lys Glu Asn Cys Tyr Leu Phe His Gly Pro
145                 150                 155                 160 ttt agc tgg gaa aaa aac cgg cag acc tgc caa tct ttg ggt ggc cag       528
Phe Ser Trp Glu Lys Asn Arg Gln Thr Cys Gln Ser Leu Gly Gly Gln
                165                 170                 175 tta cta caa att aat ggt gca gat gat ctg aca ttc atc tta caa gca       576
Leu Leu Gln Ile Asn Gly Ala Asp Asp Leu Thr Phe Ile Leu Gln Ala
            180                 185                 190 att tcc cat acc acc tcc ccg ttc tgg att gga ttg cat cgg aag           621
Ile Ser His Thr Thr Ser Pro Phe Trp Ile Gly Leu His Arg Lys
        195                 200                 205
```

Figure 7

```
Isoform 5
atg act ttt gat gac aag atg aag cct gcg aat gac gag cct gat gag      48
Met Thr Phe Asp Asp Lys Met Lys Pro Ala Asn Asp Glu Pro Asp Glu
1                   5                   10                  15 aag tca tgt ggc aag aag cct aaa ggt ctg cat ttg ctt tct tcc cca      96
Lys Ser Cys Gly Lys Lys Pro Lys Gly Leu His Leu Leu Ser Ser Pro
                20                  25                  30 tgg tgg ttc cct gct gct atg act ctg gtc atc ctc tgc ctg gtg ttg      144
Trp Trp Phe Pro Ala Ala Met Thr Leu Val Ile Leu Cys Leu Val Leu
            35                  40                  45 tca gtg acc ctt att gta cag tgg aca caa tgatcgtatc ctggaagggc        194
Ser Val Thr Leu Ile Val Gln Trp Thr Gln
        50                  55 agatgttagc ccagcagaag gcagaaaaca cttcacagga atcaaagaag gaactgaaag    254
gaaagataga caccctcacc cagaagctga acgactccaa agagcaggag gagctacacc   314 cccccgaac ctccaagaag ccctgcaaag agctgcaaac tcttcaggtc cttgtccaca    374
agactggctc tggcataaag aaaactgtta cctcttccat gggccttta gctgggaaaa   434 aaaccggcag acctgccaat ctttgggtgg gcagttacta caaattaatg gtgcagatga   494
tctgacattc atcttacaag caatttccca taccacctcc ccttcttgga ttggattgca   554
tcggaagaag cctggcaacc atgggtatgg gagaatggac ttctttgaat tttaattttt   614
aagacagggc gtttttacag ttttttcataa ggacttgtga tacttagagg ctgggttcg   674 ttgaaatgat tctattggtt agcatgtaga aaaaaatt
```

Figure 8

```
Isoform 6
atg act ttt gat gac aag atg aag cct gcg aat gac gag cct gat cag      48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca      96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg     144
Trp Trp Phe Pro Ala Ala Met Thr Leu Val Ile Leu Cys Leu Val Leu
        35                  40                  45 tca gtg acc ctt att gta cag tgg aca caa taggagtccc agagagaact       194
Ser Val Thr Leu Ile Val Gln Trp Thr Gln
        50                  55 caagggaaag atagacaccc tcaccttgaa gctgaacgag aaatccaaag agcaggagga   254
gcttctacag aagaatcaga acctccaaga agcctgcaa agagctgcaa acttttcagg    314
tccttgtcca caagactggc tctggcataa agaaaactgt tacctcttcc atgggccctt   374
tagctgggaa aaaaaccggc agacctgcca atctttgggt ggccagttac tacaaattaa   434
tggtgcagat gatctgacat tcatcttaca agcaatttcc cataccacct cccgttctg    494 gattggattg catcggaaga agcctggcca accatggcta tgggagaatg gaactccttt   554
gaatttccaa ttctttaaga ccagggcgt ttctttacag ctatattcat caggcaactg    614
tgcataccct caagacggac tgtgttcgct gaaaactgca ttctaattgc attcagcata   674
tgtcaaaaga agacaaatca tttgcaaatt tagtgaatct aaagaat                 721
```

Figure 9

Isoform 7

```
atg act ttt gat gac aag atg aag cct gcg aat gac gag cct gat cag      48
Met Thr Phe Asp Asp Lys Met Lys Pro Ala Asn Asp Glu Pro Asp Gln
1               5                   10                  15 aag tca tgt ggc aag aag cct aaa gag gag tcc cag aga gaa ctc aag      96
Lys Ser Cys Gly Lys Lys Pro Lys Glu Glu Ser Gln Arg Glu Leu Lys
                20                  25                  30 gga aag ata gac acc atc acc cgg aag ctg gac gag aaa tcc aaa gag     144
Gly Lys Ile Asp Thr Ile Thr Arg Lys Leu Asp Glu Lys Ser Lys Glu
            35                  40                  45 cag gag gag ctt ctg cag atg att cag aac ctc caa gaa gcc ctg cag     192
Gln Glu Glu Leu Leu Gln Met Ile Gln Asn Leu Gln Glu Ala Leu Gln
        50                  55                  60 aga gct gca aac tct tca gag gag tcc cag aga gaa ctc aag gga aag     240
Arg Ala Ala Asn Ser Ser Glu Glu Ser Gln Arg Glu Leu Lys Gly Lys
65                  70                  75                  80 ata gac acc ctc acc ttg aag ctg aac gag aaa tcc aaa gag cag gag     288
Ile Asp Thr Leu Thr Leu Lys Leu Asn Glu Lys Ser Lys Glu Gln Glu
                85                  90                  95 gag ctt cta cag aag aat cag aac ctc caa gaa gcc ctg caa aga gct     336
Glu Leu Leu Gln Lys Asn Gln Asn Leu Gln Glu Ala Leu Gln Arg Ala
            100                 105                 110 gca aac ttt tca ggt cct tgt cca caa gac tgg ctc tgg cat aaa gaa     384
Ala Asn Phe Ser Gly Pro Cys Pro Gln Asp Trp Leu Trp His Lys Glu
        115                 120                 125 aac tgt tac ctc ttc cat ggg ccc ttt ggc tgg gaa aaa aac cgg cag     432
Asn Cys Tyr Leu Phe His Gly Pro Phe Gly Trp Glu Lys Asn Arg Gln
130                 135                 140 acc tgc caa tct ttg ggt ggc cag tta cta caa att aat ggt gca gat     480
Thr Cys Gln Ser Leu Gly Gly Gln Leu Leu Gln Ile Asn Gly Ala Asp
145                 150                 155                 160 gat ctg aca ttc atc tta caa gca att tcc cat acc acc tcc cca ttc     528
Asp Leu Thr Phe Ile Leu Gln Ala Ile Ser His Thr Thr Ser Pro Phe
                165                 170                 175 tgg att gga ttg cat cgg aag aag cct ggc caa cca tgg cta tgg gag     576
Trp Ile Gly Leu His Arg Lys Lys Pro Gly Gln Pro Trp Leu Trp Glu
            180                 185                 190 aat gga act cct ttg aat ttt caa ttc ttt aag acc agg ggc gtt tct     624
Asn Gly Thr Pro Leu Asn Phe Gln Phe Phe Lys Thr Arg Gly Val Ser
        195                 200                 205 tta cag cta tat tca tca agc aac tgt gca tac ctt caa gac gga gct     672
Leu Gln Leu Tyr Ser Ser Ser Asn Cys Ala Tyr Leu Gln Asp Gly Ala
210                 215                 220 gtg ttc gct gaa aac tgc att cta att gca ttc agc ata tgt cag aag     720
Val Phe Ala Glu Asn Cys Ile Leu Ile Ala Phe Ser Ile Cys Gln Lys
225                 230                 235                 240 aag aca aat cat ttg caa att tag                                      744
Lys Thr Asn His Leu Gln Ile
                245
```

Figure 10

Isoform 8

```
atg act ttt gat gac aag atg aag cct gcg aat gac gag cct gat cag       48
Met Thr Phe Asp Asp Lys Met Lys Pro Ala Asn Asp Glu Pro Asp Gln
1                   5                  10                  15 aag tca tgt ggc aag aag cct aaa gag gag tcc cag aga gaa ctc aag       96
Lys Ser Cys Gly Lys Lys Pro Lys Glu Glu Ser Gln Arg Glu Leu Lys
                20                  25                  30 gga aag ata gac acc ctc acc ttg aag ctg aac gag aaa tcc aaa gag      144
Gly Lys Ile Asp Thr Leu Thr Leu Lys Leu Asn Glu Lys Ser Lys Glu
            35                  40                  45 cag gag gag ctt cta cag aag aat cag aac ctc caa gaa gcc ctg caa      192
Gln Glu Glu Leu Leu Gln Lys Asn Gln Asn Leu Gln Glu Ala Leu Gln
        50                  55                  60 aga gct gca aac ttt tca ggt cct tgt cca caa gac tgg ctt tgg cat      240
Arg Ala Ala Asn Phe Ser Gly Pro Cys Pro Gln Asp Trp Leu Trp His
65                  70                  75                  80 aaa gaa aac tgt tac ctc ttc cat ggg ccc ttt agc tgg gaa aaa aac      288
Lys Glu Asn Cys Tyr Leu Phe His Gly Pro Phe Ser Trp Glu Lys Asn
                85                  90                  95 cgg cag acc tgc caa tct ttg ggt ggc cag tta cta caa att aat ggt      336
Arg Gln Thr Cys Gln Ser Leu Gly Gly Gln Leu Leu Gln Ile Asn Gly
                100                 105                 110 gca gat gat ctg aca ttc atc tta caa gca att tcc cat acc acc tcc      384
Ala Asp Asp Leu Thr Phe Ile Leu Gln Ala Ile Ser His Thr Thr Ser
            115                 120                 125 cca ttc tgg att gga ttg cat cgg aag aag cct ggc caa cca tgg cta      432
Pro Phe Trp Ile Gly Leu His Arg Lys Lys Pro Gly Gln Pro Trp Leu
        130                 135                 140 tgg gag aat gga act cct ttg aat ttt caa ttt ttt aag acc agg ggc      480
Trp Glu Asn Gly Thr Pro Leu Asn Phe Gln Phe Phe Lys Thr Arg Gly
145                 150                 155                 160 gtt tct tta cag cta tat tca tca ggc aat tgt gca tac ctt caa gac      528
Val Ser Leu Gln Leu Tyr Ser Ser Gly Asn Cys Ala Tyr Leu Gln Asp
                165                 170                 175 gga gct gtg ttc gct gaa aac tgc att cta att gca ttc agc ata tgt      576
Gly Ala Val Phe Ala Glu Asn Cys Ile Leu Ile Ala Phe Ser Ile Cys
                180                 185                 190 cag aag aag aca aat cat ttg caa att tag                              606
Gln Lys Lys Thr Asn His Leu Gln Ile
                195                 200
```

Figure 11

```
Isoform 9
atg act ttt gat gac aag atg aag cct gcg aat gac gag cct gat cag      48
Met Thr Phe Asp Asp Lys Met Lys Pro Ala Asn Asp Glu Pro Asp Gln
1               5                   10                  15 aag tca tgt ggc aag aag cct aaa ggt cct tgt cca caa gac tgg ctc      96
Lys Ser Cys Gly Lys Lys Pro Lys Gly Pro Cys Pro Gln Asp Trp Leu
                20                  25                  30 tgg cat aaa gaa aac tgt tac ctc ttc cat ggg ccc ttt agc tgg gaa     144
Trp His Lys Glu Asn Cys Tyr Leu Phe His Gly Pro Phe Ser Trp Glu
        35                  40                  45 aaa aac cgg cag acc tgc caa tct ttg ggt ggc cag tta cta caa att     192
Lys Asn Arg Gln Thr Cys Gln Ser Leu Gly Gly Gln Leu Leu Gln Ile
50                  55                  60 aat ggt gca gat gat ctg aca ttc atc tta caa gca att tcc cat acc     240
Asn Gly Ala Asp Asp Leu Thr Phe Ile Leu Gln Ala Ile Ser His Thr
65              70                  75                  80 acc tcc cca ttc tgg att gga ttg cat cgg aag aag cct ggc caa cca     288
Thr Ser Pro Phe Trp Ile Gly Leu His Arg Lys Lys Pro Gly Gln Pro
                85                  90                  95 tgg cta tgg gag aat gga act cct ttg aat ttt caa ttc ttt aag acc     336
Trp Leu Trp Glu Asn Gly Thr Pro Leu Asn Phe Gln Phe Phe Lys Thr
                100                 105                 110 agg ggc gtt tct tta cag cta tat tca tca ggc aac tgt gca tac ctt     384
Arg Gly Val Ser Leu Gln Leu Tyr Ser Ser Gly Asn Cys Ala Tyr Leu
        115                 120                 125 caa gac gga gct gtg ttc gct gaa aac tgc att cta att gca ttc agc     432
Gln Asp Gly Ala Val Phe Ala Glu Asn Cys Ile Leu Ile Ala Phe Ser
        130                 135                 140 ata tgt cag aag aag aca aat cat ttg caa att tag                     468
Ile Cys Gln Lys Lys Thr Asn His Leu Gln Ile
145                 150                 155
```

Figure 12

A.
```
Isoform 1 (R1)  ESKKELKGKIDTLTQKLNEKSKEQEELLQKNQNLQEALQRAANSSE
Isoform 1 (R2)  ESQRELKGKIDTITRKLDEKSKEQEELLQMIQNLQEALQRAANSSE
Isoform 1 (R3)  ESQRELKGKIDTLTLKLNEKSKEQEELLQKNQNLQEALQRAANFSG
Isoform 3 (R1)  QSKKELKGKIDTLTQKLNEKSKEQEELLQKNQNLQEALQRAANSSE
Isoform 3 (R3)  ESQRELKGKIDTLTLKLNEKSKEQ...
Isoform 4 (R1)  ESKKELKGKIDTLTQKLNEKSKEQEELLQKNQNLQEALQRAANFSG
Isoform 7 (R2)  ESQRELKGKIDTITRKLDEKSKEQEELLQMIQNLQEALQRAANSSE
Isoform 7 (R3)  ESQRELKGKIDTLTLKLNEKSKEQEELLQKNQNLQEALQRAANFSG
Isoform 8 (R3)  ESQRELKGKIDTLTLKLNEKSKEQEELLQKNQNLQEALQRAANFSG
                 -  ------- -  -- ------------   -------------- -
```

B.
```
Isoform 1 (R1)  ESKKELKGKIDTLTQKLNEKSKEQEELLQKNQNLQEALQRAANSSE
Isoform 3 (R1)  QSKKELKGKIDTLTQKLNEKSKEQEELLQKNQNLQEALQRAANSSE
Isoform 4 (R1)  ESKKELKGKIDTLTQKLNEKSKEQEELLQKNQNLQEALQRAANFSG
                 --------------------------------------------- -
```

C.
```
Isoform 1 (R2)  ESQRELKGKIDTITRKLDEKSKEQEELLQMIQNLQEALQRAANSSE
Isoform 7 (R2)  ESQRELKGKIDTITRKLDEKSKEQEELLQMIQNLQEALQRAANSSE
                ---------------------------------------------
```

D.
```
Isoform 1 (R3)  ESQRELKGKIDTLTLKLNEKSKEQEELLQKNQNLQEALQRAANFSG
Isoform 3 (R3)  ESQRELKGKIDTLTLKLNEKSKEQ...
Isoform 7 (R3)  ESQRELKGKIDTLTLKLNEKSKEQEELLQKNQNLQEALQRAANFSG
Isoform 8 (R3)  ESQRELKGKIDTLTLKLNEKSKEQEELLQKNQNLQEALQRAANFSG
                ---------------------------------------------
```

E.
```
Isoform 1 (R1)  ESKKELKGKIDTLTQKLNEKSKEQEELLQKNQNLQEALQRAANSSE
Isoform 1 (R2)  ESQRELKGKIDTITRKLDEKSKEQEELLQMIQNLQEALQRAANSSE
Isoform 1 (R3)  ESQRELKGKIDTLTLKLNEKSKEQEELLQKNQNLQEALQRAANFSG
Isoform 3 (R1)  QSKKELKGKIDTLTQKLNEKSKEQEELLQKNQNLQEALQRAANSSE
Isoform 3 (R3)  ESQRELKGKIDTLTLKLNEKSKEQ...
Isoform 4 (R1)  ESKKELKGKIDTLTQKLNEKSKEQEELLQKNQNLQEALQRAANFSG
Isoform 7 (R2)  ESQRELKGKIDTITRKLDEKSKEQEELLQMIQNLQEALQRAANSSE
Isoform 7 (R3)  ESQRELKGKIDTLTLKLNEKSKEQEELLQKNQNLQEALQRAANFSG
Isoform 8 (R3)  ESQRELKGKIDTLTLKLNEKSKEQEELLQKNQNLQEALQRAANFSG
human           ESENELKEMIETLARKLNEKSKEQMELHHQNLNLQETLKRVANCSA
                 -  ---  -  -  -- ------  --   ----  -  -- -
```

ATHEROSCLEROSIS SUSCEPTIBILITY GENE LOCUS 1 (ATHSQ1) AND ATHEROSCLEROSIS SUSCEPTIBILITY GENE LOCUS 2 (ATHSQ2)

The invention disclosed herein was made with Government support under grant numbers HL-09930, HL-54591, and HL-22682 from the National Institutes of Health, U.S. Department of Health and Human Services. Accordingly, the U.S. Government has certain rights in this invention.

BACKGROUND OF THE INVENTION

Throughout this application, various publications are referenced by author and year. Citations for these references may be found at the end of the specification immediately preceding the claims. The disclosures of these publications in their entireties are hereby incorporated by reference into this application to describe more fully the art to which this invention pertains.

The genetics of atherosclerosis has been the focus of intense investigation. A subset of cases is caused by uncommon Mendelian mutations that predispose individuals to atherosclerosis (Breslow 2000; Keating and Sanguinetti 1996; Lifton 1996). The mutated genes include low-density lipoprotein receptor (LDLR) (Hobbs et al. 1992), cystathionine beta-synthase (CBS) (Kraus 1999), and, in some cases, ATP-binding cassette-A1 (Bodzioch et al. 1999; Brooks-Wilson et al. 1999; Rust et al. 1999) among others. Identification of these genes has shed light on biochemical pathways involved in atherogenesis and provided the basis for current therapeutic interventions. However, the common forms of atherosclerosis are multifactorial in origin. Attempts to map the common susceptibility loci have been hampered by genetic heterogeneity, polygenic inheritance, incomplete pedigrees, and environmental influences. The fact that few of the genome-wide linkage studies have reported loci with large effects points to the existence of multiple loci each having small to moderate effects (Aouizerat et al. 1999; Hixson and Blangero 2000; Rice et al. 2000; Shearman 2000). The modest nature of susceptibility gene effects will likely require extremely large sample sizes or very densely-spaced genetic markers for successful linkage mapping (Risch and Merikangas 1996).

Mouse models offer significant advantages for genetic dissection of complex diseases. The ability to perform selective breeding, produce many offspring, determine inheritance of alleles without ambiguity, and control the environment is a critical factor. Early studies of murine atherosclerosis indicated that there was a clear genetic component. Inbred strains of mice exhibited a spectrum of aortic fatty streak lesion areas following the feeding of atherogenic diets high in cholesterol, fat, and cholic acid (Paigen et al. 1985; Qiao et al. 1994; Roberts and Thompson 1977). A number of susceptibility loci (Ath1–8) were reported based on phenotypic analyses of recombinant inbred strains derived from "resistant" and "susceptible" parents (Paigen 1995; Paigen et al. 1987, 1989; Stewart-Phillips et al. 1989). Although these studies were instrumental in pointing out strain-specific variations, none of the loci have been confirmed by more rigorous analyses of large genetic crosses.

A shortcoming of the diet-fed, inbred mouse model (in terms of carrying out quantitative genetic studies) is that aortic lesion development is minimal even in susceptible strains. Recently, Dansky et al. (1999) showed that the strain-related differences in susceptibility could be accentuated when a gene-targeted disease model was employed. Thus, C57BL/6J mice homozygous for the apolipoprotein E knockout allele exhibited 7–9 fold greater aortic root lesion area relative to FVB/NJ mice homozygous for the allele without any overlap of the phenotypic values. To provide candidate susceptibility loci for human atherosclerosis, we have performed a genome scan of an interspecific cross using the low-density lipoprotein receptor knockout model (Ishibashi et al. 1993). In this model, feeding of a Western-style diet results in elevated plasma LDL levels (similar to levels in humans) and development of human-like complicated fibrous plaques (Masucci-Magoulas et al. 1997). Two significant susceptibility loci were localized to chromosome (Chr) 4 and 6. The effects of these loci were independent of common risk factors for human disease including plasma lipoprotein levels, plasma insulin levels, and body weight.

SUMMARY OF THE INVENTION

This invention provides an isolated nucleic acid encoding a mammalian LOX-1 receptor protein, wherein the receptor protein comprises consecutive amino acids having the following sequence: —S, X, X, E, L, K, X, X, I, X, T, X, X, X, K, L, X, E, K, S, K, E, Q, X, E, L, X, X, X, X, X, N, L, Q, E, X, L, X, R, X, A, N, X, S— (SEQ ID NO: 39), wherein X is any amino acid.

The invention provides an isolated nucleic acid encoding a mammalian membrane-bound LOX-1 receptor protein, wherein the nucleic acid encodes a protein selected from the group consisting of:
 (a) a LOX-1 receptor protein comprising consecutive amino acids having a sequence identical to that set forth for Isoform 1 in SEQ ID NO: 20,
 (b) a LOX-1 receptor protein comprising consecutive amino acids having a sequence identical to that set forth for Isoform 3 in SEQ ID NO: 24, and
 (c) a LOX-1 receptor protein comprising consecutive amino acids having a sequence identical to that set forth for Isoform 4 in SEQ ID NO: 26.

The invention provides an isolated nucleic acid encoding a mammalian soluble LOX-1 receptor protein, wherein the nucleic acid encodes a protein selected from the group consisting of:
 (a) a LOX-1 receptor protein comprising consecutive amino acids having a sequence identical to that set forth for Isoform 7 in SEQ ID NO: 14,
 (b) a LOX-1 receptor protein comprising consecutive amino acids having a sequence identical to that set forth for Isoform 8 in SEQ ID NO: 16, and
 (c) a LOX-1 receptor protein comprising consecutive amino acids having a sequence identical to that set forth for Isoform 9 in SEQ ID NO: 18.

The invention provides an isolated nucleic acid encoding a mammalian LOX-1 receptor protein, wherein the nucleic acid comprises:
 (a) a nucleic acid sequence given in any one of SEQ ID Nos: 13, 15, 17, 19, 21, 23, 25, 27, or 28; or
 (b) a nucleic acid sequence degenerate to a sequence of (a) as a result of the genetic code.

The invention provides a method involving competitive binding for identifying a chemical compound which specifically binds to a mammalian LOX-1 receptor, which comprises contacting cells expressing on their cell surface the mammalian LOX-1 receptor with both the chemical compound and a second chemical compound known to bind to the receptor, and separately with only the second chemical compound, under conditions suitable for binding of both compounds, and measuring specific binding of the second chemical compound to the mammalian LOX-1 receptor, a decrease in the binding of the second chemical compound to the mammalian LOX-1 receptor in the presence of the chemical compound indicating that the chemical compound binds to the mammalian LOX-1 receptor.

The invention provides a method of screening a plurality of chemical compounds not known to bind to a mammalian LOX-1 receptor to identify a compound which specifically binds to the mammalian LOX-1 receptor, which comprises:

(a) contacting cells expressing on their cell surface the mammalian LOX-1 receptor with the plurality of compounds not known to bind specifically to the mammalian LOX-1 receptor, under conditions permitting binding of compounds known to bind to the mammalian LOX-1 receptor;

(b) determining whether the binding of a compound known to bind to the mammalian LOX-1 receptor is reduced in the presence of the compounds within the plurality of compounds, relative to the binding of the compound in the absence of the plurality of compounds; and if so (c) separately determining the binding to the mammalian LOX-1 receptor of compounds included in the plurality of compounds, so as to thereby identify the compound which specifically binds to the mammalian LOX-1 receptor.

The invention provides a method of identifying a compound which activates a mammalian LOX-1 receptor which comprises contacting cells expressing on their cell surface the mammalian LOX-1 receptor with the compound under conditions permitting activation of the LOX-1 receptor, and detecting activation of the LOX-1 receptor, thereby identifying the compound as a compound which activates a mammalian LOX-1 receptor.

The invention provides a method of identifying a compound which inhibits the activity of a mammalian LOX-1 receptor which comprises contacting cells expressing on their cell surface the mammalian LOX-1 receptor with the compound under conditions permitting inhibition of the activity of the LOX-1 receptor, and detecting inhibition of the activity of the LOX-1 receptor, thereby identifying the compound as a compound which inhibits the activity of a mammalian LOX-1 receptor.

The invention provides a method of screening a plurality of chemical compounds not known to activate a mammalian LOX-1 receptor to identify a compound which activates the mammalian LOX-1 receptor which comprises:

(a) contacting cells expressing on their cell surface the mammalian LOX-1 receptor with the plurality of compounds not known to activate the mammalian LOX-1 receptor, under conditions permitting activation of the mammalian LOX-1 receptor;

(b) determining whether the activity of the mammalian LOX-1 receptor is increased in the presence of the compounds; and if so (c) separately determining whether the activation of the mammalian LOX-1 receptor is increased by each compound included in the plurality of compounds, so as to thereby identify the compound which activates the mammalian LOX-1 receptor.

The invention provides a method of screening a plurality of chemical compounds not known to inhibit the activity of a mammalian LOX-1 receptor to identify a compound which inhibits the activity of the mammalian LOX-1 receptor, which comprises:

(a) contacting cells expressing on their cell surface the mammalian LOX-1 receptor with the plurality of compounds in the presence of a known compound which activates the mammalian LOX-1 receptor, under conditions permitting activation of the mammalian LOX-1 receptor;

(b) determining whether the activity of the mammalian LOX-1 receptor is reduced in the presence of the plurality of compounds, relative to the activity of the mammalian LOX-1 receptor in the absence of the plurality of compounds; and if so (c) separately determining the inhibition of activity of the mammalian LOX-1 receptor for each compound included in the plurality of compounds, so as to thereby identify the compound which inhibits the activity of the mammalian LOX-1 receptor.

The invention provides a method of treating or preventing atherosclerosis in a subject which comprises administering to the subject an amount of a compound effective to decrease the activity of a mammalian LOX-1 receptor and treat atherosclerosis in the subject.

The invention provides a method of determining the susceptibility of a subject to atherosclerosis, which comprises detecting soluble LOX-1 receptor in the subject's plasma, wherein the presence of soluble LOX-1 receptor indicates an decreased susceptibility to atherosclerosis and an absence of soluble LOX-1 receptor indicates an increased susceptibility to atherosclerosis.

The invention provides a method of treating inflamation in a subject which comprises administering to the subject an amount of a soluble mammalian LOX-1 receptor effective to treat inflamation in the subject.

The invention provides a method of treating inflammation in a subject which comprises administering to the subject an amount of a compound effective to decrease the activity of a mammalian LOX-1 receptor and treat inflammation in the subject.

The invention provides a method of treating an abnormality in a subject wherein the abnormality is alleviated by decreasing the activity of a mammalian LOX-1 receptor, which comprises administering to the subject an amount of a compound effective to decrease the activity of the LOX-1 receptor, thereby treating the abnormality.

The invention provides a method of treating an abnormality in a subject wherein the abnormality is alleviated by decreasing LOX-1 signal transduction, which comprises administering to the subject an amount of a soluble mammalian LOX-1 receptor effective to bind LOX-1 receptor ligand and reduce availability of LOX-1 receptor ligand to bind to a membrane-bound LOX-1 receptor, thereby decreasing LOX-1 signal transduction and treating the abnormality.

BRIEF DESCRIPTION OF THE FIGURES

FIG. 1. Distribution of fatty streak lesion areas among 174 Mbc-Ldlr0 mice grouped by sex. Mice were fed a Western-type diet for three months. Values are expressed as $\mu m^2$/section. Solid horizontal bars represent the range of values for sex- and age-matched B6-Ldlr0 controls (N=6 for each sex).

FIGS. 3A–3C. Sequence alignment of mouse LOX-1 coding regions. LOX-1C primers were used to clone LOX-1 coding regions from macrophage cDNAs by polymerase chain reaction. Alignment in DIALIGN format.
Aligned sequences:
   B-Isoform 1 (B6-Isoform 1), rat lox-like (SEQ ID NO: 11);
   M-Isoform 1 (MOLF-Isoform 1), rat lox-like (SEQ ID NO: 12);
   Isoform 7, soluble (SEQ ID NO: 13);
   Isoform 8, soluble (SEQ ID NO: 15);
   Isoform 9, soluble (SEQ ID NO: 17).
TM=transmembrane domain. $1^{st}$, $2^{nd}$, and $3^{rd}$ repeat=copies of a unique repetitive region.

FIGS. 4A–4B. Nucleotide and amino acid sequences for LOX-1 Isoform 1 (SEQ ID NO: 19 and 20, respectively).

FIG. 5. Nucleotide and amino acid sequences for LOX-1 Isoform 2 (SEQ ID NO: 21 and 22, respectively). The amino acid sequence is the same for isoforms 2, 5, and 6.

FIG. 6. Nucleotide and amino acid sequences for LOX-1 Isoform 3 (SEQ ID NO: 23 and 24, respectively).

FIG. 7. Nucleotide and amino acid sequences for LOX-1 Isoform 4 (SEQ ID NO: 25 and 26, respectively).

FIG. 8. Nucleotide and amino acid sequences for LOX-1 Isoform 5 (SEQ ID NO: 27 and 22, respectively). The amino acid sequence is the same for isoforms 2, 5, and 6.

FIG. 9. Nucleotide and amino acid sequences for LOX-1 Isoform 6 (SEQ ID NO: 28 and 22, respectively). The amino acid sequence is the same for isoforms 2, 5, and 6.

FIG. 10. Nucleotide and amino acid sequences for LOX-1 Isoform 7 (SEQ ID NO: 13 and 14, respectively).

FIG. 11. Nucleotide and amino acid sequences for LOX-1 Isoform 8 (SEQ ID NO: 15 and 16, respectively).

FIG. 12. Nucleotide and amino acid sequences for LOX-1 Isoform 9 (SEQ ID NO: 17 and 18, respectively).

FIGS. 13A–13E. Alignment of amino acid sequences of LOX-1 repeat motifs.
   A. Alignment of 46 amino acid repeat motifs (R1, R2, and R3) for Isoforms 1, 3, 4, 7, and 8. The sequence for Isoform 3 is incomplete. Isoforms 2, 5, 6, and 9 do not contain repeats. The dashed lines beneath the sequence alignment indicate positions where there is 100% identity among the sequences. Isoform 1 (R1), SEQ ID NO: 29; Isoform 1 (R2), SEQ ID NO: 30; Isoform 1 (R3), SEQ ID NO: 31; Isoform 3 (R1), SEQ ID NO: 32; Isoform 3 (R3), SEQ ID NO: 33; Isoform 4 (R1), SEQ ID NO: 34; Isoform 7 (R2), SEQ ID NO: 35; Isoform 7 (R3), SEQ ID NO: 36; Isoform 8 (R3), SEQ ID NO: 37.
   B.–D. The sequences from A are aligned for repeat 1 (R1) in B, repeat 2 (R2) in C, and repeat 3 (R3) in D.
   E. The repeat motifs encoded by macrophage-derived isoforms of mouse LOX-1 from A are aligned with a homologous region encoded by endothelial-derived human LOX-1. The human region (SEQ ID NO: 38) does not repeat. Human sequence from Sawamura et al. (1997).

DETAILED DESCRIPTION OF THE INVENTION

Figure 2:
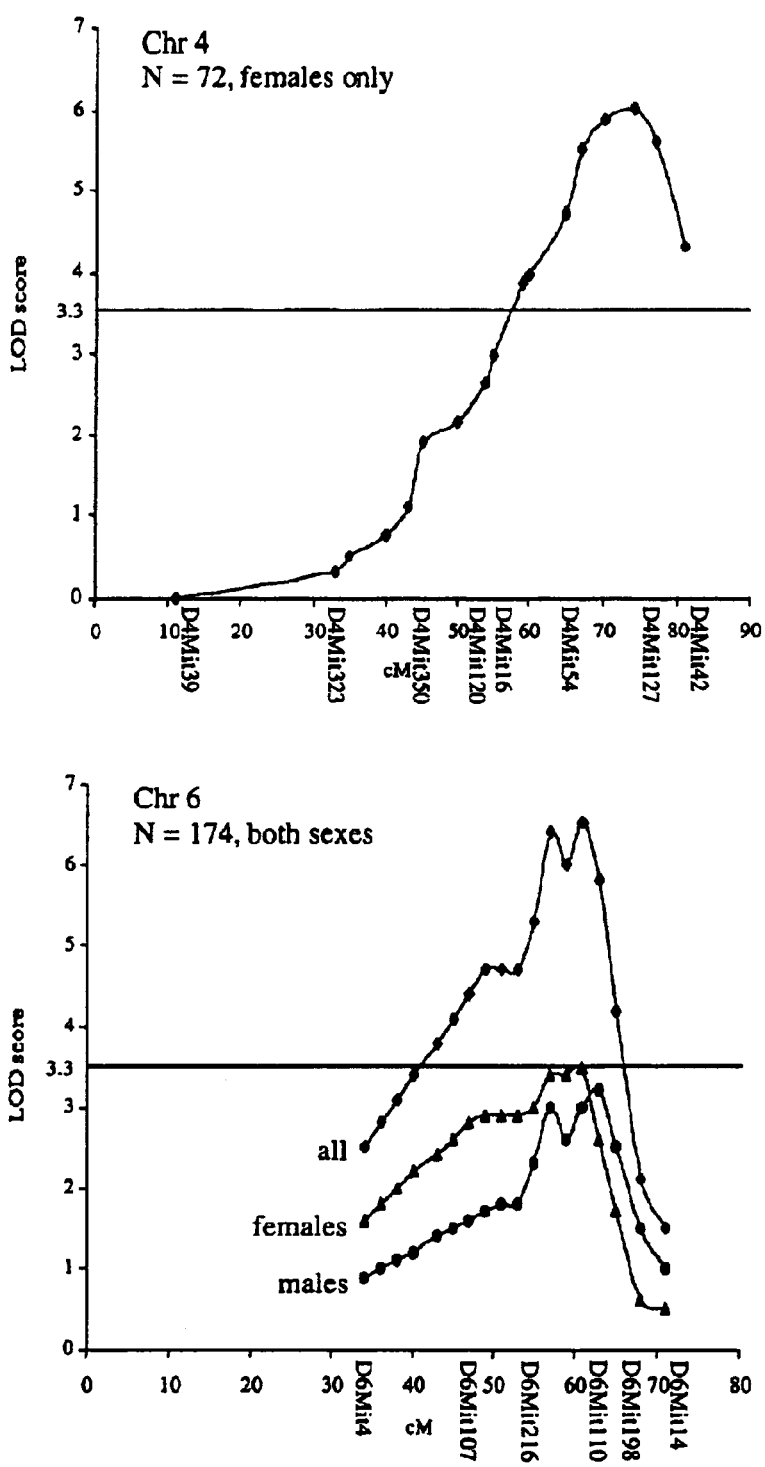
FIG. 2. LOD score plots for Chr 4 and Chr 6 lesion susceptibility QTLs. The y-axis indicates LOD scores; the x-axis indicates position along the chromosome (distance from the centromere in centiMorgans, cM). Microsatellite markers typed in Mbc-Ldlr0 mice are indicated below the x-axis. LOD scores were calculated and plotted at 2-cM intervals using Map Manager QT software. The significance threshold of p=0.05 for a backcross is indicated by a solid line at LOD=3.3.

Throughout this application, the following standard abbreviations are used to indicate specific amino acids:

| 3-character abbreviation | Amino Acid | 1-character abbreviation |
|---|---|---|
| Ala | Alanine | A |
| Arg | Arginine | R |
| Asn | Asparagine | N |
| Asp | Aspartic Acid | D |
| Cys | Cysteine | C |
| Gln | Glutamine | Q |
| Glu | Glutamic Acid | E |
| Gly | Glycine | G |
| His | Histidine | H |
| Ile | Isoleucine | I |
| Leu | Leucine | L |
| Lys | Lysine | K |
| Met | Methionine | M |
| Phe | Phenylalanine | F |
| Pro | Proline | P |
| Ser | Serine | S |
| Thr | Threonine | T |
| Trp | Tryptophane | W |
| Tyr | Tyrosine | Y |
| Val | Valine | V |
| Asx | Asparagine/ Aspartic Acid | B |
| Glx | Glutamine/ Glutamic Acid | Z |
| *** | (End) | * |
| Xxx | Any amino acid or as specified. | X |

The following standard abbreviations are used to indicate specific nucleotide bases:
   A=adenine;
   C=cytosine;
   G=guanine;
   T=thymine.

The following definitions are presented as an aid in understanding this invention:
   Chr, chromosome;
   cM, centiMorgans;
   HDL, high density lipoprotein;
   LDL, low density lipoprotein;
   Ldlr, low density lipoprotein receptor;
   LOD, logarithm of odds;
   LOX-1, oxidized low density lipoprotein receptor
   Olr1, oxidized low density lipoprotein receptor
   MGD, Mouse Genome Database;
   QTL, quantitative trait locus.
   "inhibiting LOX-1 activity", examples include, without limitation, interfering with or blocking ligand binding to and activation of the receptor;
   "treating" a subject, examples include, without limitation, reversing, slowing, stabilizing or otherwise ameliorating a disease or disorder with which the subject is afflicted;
   "inhibit onset" of a disorder, examples include, without limitation, lessening the likelihood of onset, delaying the onset, or preventing the onset.

Having due regard to the preceding definitions, this invention provides an isolated nucleic acid encoding a protein comprising an amino acid sequence selected from the group consisting of SEQ ID NO: 14, SEQ ID NO: 16, SEQ ID NO: 18, SEQ ID NO: 22, SEQ ID NO: 24, and SEQ ID NO: 26. In different embodiments, the nucleic acid has a sequence selected from the group consisting of SEQ ID NO: 13, SEQ ID NO: 15, SEQ ID NO: 17, SEQ ID NO: 21, SEQ ID NO: 23, SEQ ID NO: 25, SEQ ID NO: 27, and SEQ ID NO: 28.

The invention provides an isolated nucleic acid encoding a mammalian LOX-1 receptor protein, wherein the receptor protein comprises consecutive amino acids having the following sequence: —S, X, X, E, L, K, X, X, I, X, T, X, X, X, K, L, X, E, K, S, K, E, Q, X, E, L, X, X, X, X, X, N, L, Q, E, X, L, X, R, X, A, N, X, S— (SEQ ID NO: 39), wherein X is any amino acid.

In one embodiment, the receptor protein comprises consecutive amino acids having the following sequence: —S, K or Q or E, K or R or N, E, L, K, G or E, K or M, I, D or E, T, L or I, T or A, Q or R or L, K, L, N or D, E, K, S, K, E, Q, E or M, E, L, L or H, Q or H, K or M or Q, N or I, Q or L, N, L, Q, E, A or T, L, Q or K, R, A or V, A, N, S or F or C, S— (SEQ ID NO: 40).

The invention provides an isolated nucleic acid encoding a mammalian membrane-bound LOX-1 receptor protein, wherein the nucleic acid encodes a protein selected from the group consisting of:
 (a) a LOX-1 receptor protein comprising consecutive amino acids having a sequence identical to that set forth for Isoform 1 in SEQ ID NO: 20,
 (b) a LOX-1 receptor protein comprising consecutive amino acids having a sequence identical to that set forth for Isoform 3 in SEQ ID NO: 24, and
 (c) a LOX-1 receptor protein comprising consecutive amino acids having a sequence identical to that set forth for Isoform 4 in SEQ ID NO: 26.

The invention provides an isolated nucleic acid encoding a mammalian soluble LOX-1 receptor protein, wherein the nucleic acid encodes a protein selected from the group consisting of:
 (a) a LOX-1 receptor protein comprising consecutive amino acids having a sequence identical to that set forth for Isoform 7 in SEQ ID NO: 14,
 (b) a LOX-1 receptor protein comprising consecutive amino acids having a sequence identical to that set forth for Isoform 8 in SEQ ID NO: 16, and
 (c) a LOX-1 receptor protein comprising consecutive amino acids having a sequence identical to that set forth for Isoform 9 in SEQ ID NO: 18.

The invention provides an isolated nucleic acid encoding a mammalian LOX-1 receptor protein, wherein the nucleic acid comprises:
 (a) a nucleic acid sequence given in any one of SEQ ID Nos: 13, 15, 17, 19, 21, 23, 25, 27, or 28; or
 (b) a nucleic acid sequence degenerate to a sequence of (a) as a result of the genetic code.

In different embodiments of any of the isolated nucleic acids described herein, the nucleic acid is DNA or RNA. In different embodiments, the DNA is cDNA, genomic DNA, or synthetic DNA.

In one embodiment of any of the isolated nucleic acids described herein, the nucleic acid molecule encodes a mouse LOX-1 receptor or a human LOX-1 receptor.

This invention provides a nucleic acid probe of at least about 15 nucleotides in length which specifically hybridizes with a nucleic acid encoding a mammalian LOX-1 receptor or with a nucleic acid having the complementary sequence thereof. In different embodiments of the probe, the mammalian LOX-1 receptor has an amino acid sequence selected from the group consisting of SEQ ID NO: 14, SEQ ID NO: 16, SEQ ID NO: 18, SEQ ID NO: 22, SEQ ID NO: 24, and SEQ ID NO: 26. In different embodiments, the probe specifically hybridizes with a nucleic acid encoding the amino acid sequence shown in SEQ ID NO: 39. In different embodiments, the probe is labeled with a detectable marker.

This invention provides a nucleic acid probe comprising at least 15 nucleotides, which probe specifically hybridizes with and has a sequence complementary to a unique sequence present within (a) any one of the nucleic acids described herein or (b) the reverse complement thereof. In different embodiments, the nucleic acid probe is DNA, cDNA, genomic DNA, synthetic DNA or RNA.

As used herein, the phrase "specifically hybridizing" means the ability of a nucleic acid molecule to recognize a nucleic acid sequence complementary to its own and to form double-helical segments through hydrogen bonding between complementary base pairs.

This invention provides an isolated protein comprising an amino acid sequence selected from the group consisting of SEQ ID NO: 14, SEQ ID NO: 16, SEQ ID NO: 18, SEQ ID NO: 22, SEQ ID NO: 24, and SEQ ID NO: 26.

This invention provides a purified mammalian membrane-bound LOX-1 receptor protein, wherein the protein comprises consecutive amino acids having a sequence identical to the sequence set forth for Isoform 1 in SEQ ID NO: 20, or for Isoform 3 in SEQ ID NO: 24, or for Isoform 4 in SEQ ID NO: 26.

This invention provides a purified mammalian soluble LOX-1 receptor protein, wherein the protein comprises consecutive amino acids having a sequence identical to the sequence set forth for Isoform 7 in SEQ ID NO: 14, or for Isoform 8 in SEQ ID NO: 16, or for Isoform 9 in SEQ ID NO: 18.

The invention provides a purified mammalian LOX-1 receptor protein encoded by any of the isolated nucleic acids described herein.

The invention provides a method of preparing a purified mammalian LOX-1 receptor protein which comprises:
 (a) inserting any of the isolated nucleic acids encoding the protein described herein into a suitable expression vector;
 (b) introducing the resulting vector into a suitable host cell;
 (c) placing the resulting host cell in suitable conditions permitting the production of the protein;
 (d) recovering the protein so produced; and optionally
 (e) isolating and/or purifying the protein so recovered.

This invention provides a vector comprising any of the nucleic acids described herein. In different embodiments, the vector is adapted for expression of the nucleic acid in a cell and comprises regulatory elements necessary for expression of the nucleic acid in the cell operatively linked to the nucleic acid so as to permit expression thereof. In different embodiments, the cell is a bacterial, Archaeal, amphibian, yeast, fungal, insect, plant, or mammalian cell. In different embodiments, the vector is a plasmid, a baculovirus, retrovirus, or a bacteriophage.

Regulatory elements required for expression include promoter sequences to bind RNA polymerase and transcription initiation sequences for ribosome binding. For example, a bacterial expression vector includes a promoter such as the lac promoter and for transcription initiation the Shine-Dalgarno sequence and the start codon AUG. Similarly, a eukaryotic expression vector includes a heterologous or homologous promoter for RNA polymerase II, a downstream polyadenylation signal, the start codon AUG, and a termination codon for detachment of the ribosome. Such vectors may be obtained commercially or assembled from the sequences described by methods well-known in the art.

The invention provides a method of transforming a cell which comprises transfecting a host cell with any of the vectors described herein.

This invention provides a cell comprising any of the vectors described herein. This invention provides a membrane preparation isolated from any of the herein described cells. This invention also provides a soluble extract isolated from any of the herein described cells. In different embodiments, the cell is a bacterial, Archaeal, amphibian, yeast, fungal, insect, plant, or mammalian cell. In different embodiments, the amphibian cell is a *Xenopus oocyte* cell or a *Xenopus melanophore* cell. In different embodiments, the mammalian cell is a HEK293 cell, a Chinese hamster ovary (CHO) cell, a COS-7 cell, a LM(tk-) cell, a mouse embryonic fibroblast NIH-3T3 cell, a mouse Y1 cell, a 293 human embryonic kidney cell, or a HeLa cell. In different embodiments, the insect cell is an Sf9 cell, an Sf21 cell or a Trichoplusia ni 5B-4 cell.

In one embodiment, prior to being transfected with the vector the host cell does not express a mammalian LOX-1 receptor protein. In one embodiment, prior to being transfected with the vector the host cell does express a mammalian LOX-1 receptor protein. In one embodiment, but for the vector present therein, the cell would not express a mammalian LOX-1 receptor.

Methods of transforming and transfecting cells with nucleic acid to obtain cells in which the encoded protein is expressed are well known in the art (Sambrook et al. 1989). Such transformed cells may also be used to test compounds and screen compound libraries to obtain compounds which bind to the expressed protein and therefore are likely to do so in vivo.

DNA encoding proteins to be studied, including foreign proteins, can be expressed by several methods. Heterologous DNA can be stably incorporated into host cells, causing the cell to perpetually express a foreign protein. DNA to be expressed can be introduced on plasmid or bacteriophage vectors by transformation or transfection (including treatment of cells with MgCl2 or CaCl, electroporation, or natural transformation), conjugation, or transduction, often, but not necessarily, following selection for linked antibiotic resistance genes. The ensuing drug resistance can be exploited to select and maintain cells that have taken up the heterologous DNA. An assortment of resistance genes are available including but not restricted to Neomycin, Kanamycin, and Hygromycin. Genes for proteins to be studied may be expressed constitutively or their expression may be induced from regulated promoters. DNA to be expressed may be located on extrachromosomal elements, such as plasmids, on intergrated prophages, or inserted into chromosomes by homologous recombination or transposition. DNA encoding proteins to be studied can also be transiently expressed in a variety of mammalian, insect, amphibian, yeast, fungal, plant and other cells by several methods, including but not restricted to transformation, transfection, calcium phosphate-mediated, DEAE-dextran mediated, liposomal-mediated, viral-mediated, electroporation-mediated and microinjection delivery. Each of these methods may require optimization of assorted experimental parameters depending on the DNA, cell line, and the type of assay to be subsequently employed.

The invention provides an antisense oligonucleotide which specifically hybridizes to any of the RNA described herein, so as to prevent translation of the RNA. The invention provides an antisense oligonucleotide which specifically hybridizes to any of the DNA described herein. In one embodiment, the antisense oligonucleotide comprises chemically modified nucleotides or nucleotide analogues.

This invention provides an antibody capable of binding to any of the proteins described herein. In one embodiment, the antibody is a monoclonal antibody. In one embodiment, the antibody is a polyclonal antibody.

The invention provides a transgenic, nonhuman mammal expressing DNA encoding any of the mammalian LOX-1 receptors described herein. The invention provides a transgenic, nonhuman mammal comprising a homologous recombination knockout of a native LOX-1 receptor.

The invention provides a method of identifying a compound which specifically binds to a mammalian LOX-1 receptor protein which comprises contacting any of the purified LOX-1 receptor proteins described herein with the compound under conditions permitting binding of the compound to the purified LOX-1 receptor protein, and detecting the presence of any such compound specifically bound to the receptor protein, thereby identifying the compound as a compound which specifically binds to a mammalian LOX-1 receptor protein. In one embodiment, the purified LOX-1 receptor protein is embedded in a lipid bilayer.

The invention provides a method of determining whether an agent inhibits the activity of a membrane-bound mammalian LOX-1 receptor, which comprises (a) contacting the agent with the receptor under conditions which would permit the inhibition of such activity by an activity-inhibiting agent, and (b) detecting whether the agent has inhibited the activity of the LOX-1 receptor. In one embodiment, the LOX-1 receptor is a mouse receptor. In one embodiment, the LOX-1 receptor is a human receptor.

The invention provides an agent determined by any of the methods described herein to inhibit the activity of a membrane-bound mammalian LOX-1 receptor. The invention provides a composition which comprises the agent and a pharmaceutically acceptable carrier.

The invention provides a method of preparing a composition which comprises identifying an agent by any of the methods described herein, recovering the agent free of LOX-1 receptor, and admixing the agent with a pharmaceutically acceptable carrier.

The invention provides a method of identifying a compound which specifically binds to a mammalian LOX-1 receptor which comprises contacting cells expressing the LOX-1 receptor, or a membrane fraction or a soluble fraction from said cells, with the compound under conditions permitting binding of the compound to the LOX-1 receptor, and detecting the presence of any such compound specifically bound to the receptor, thereby identifying the compound as a compound which specifically binds to a mammalian LOX-1 receptor.

In one embodiment of any of the methods described herein, the cells do not normally express the mammalian LOX-1 receptor and the mammalian LOX-1 receptor is encoded by any of the isolated nucleic acids described herein.

The invention provides a method involving competitive binding for identifying a chemical compound which specifically binds to a mammalian LOX-1 receptor which comprises contacting cells expressing on their cell surface the mammalian LOX-1 receptor with both the chemical compound and a second chemical compound known to bind to the receptor, and separately with only the second chemical compound, under conditions suitable for binding of both compounds, and measuring specific binding of the second chemical compound to the mammalian LOX-1 receptor, a decrease in the binding of the second chemical compound to the mammalian LOX-1 receptor in the presence of the chemical compound indicating that the chemical compound binds to the mammalian LOX-1 receptor. In one embodiment, the second chemical compound is labeled oxidized-LDL. In one embodiment, the binding of the second chemical compound to the LOX-1 receptor is measured by quantifying the amount of labeled oxidized-LDL inside the cells. In different embodiments, oxidized-LDL is labeled with a fluorescent label, a radioactive label, or a calorimetric label. In one embodiment, oxidized-LDL is labeled with $^3$H. In one embodiment, the cells do not normally express the mammalian LOX-1 receptor and the mammalian LOX-1 receptor is encoded by any of the isolated nucleic acids described herein.

The invention provides a method of screening a plurality of chemical compounds not known to bind to a mammalian LOX-1 receptor to identify a compound which specifically binds to the mammalian LOX-1 receptor, which comprises:
(a) contacting cells expressing on their cell surface the mammalian LOX-1 receptor with the plurality of compounds not known to bind specifically to the mammalian LOX-1 receptor, under conditions permitting binding of compounds known to bind to the mammalian LOX-1 receptor;
(b) determining whether the binding of a compound known to bind to the mammalian LOX-1 receptor is reduced in the presence of the compounds within the plurality of compounds, relative to the binding of the compound in the absence of the plurality of compounds; and if so
(c) separately determining the binding to the mammalian LOX-1 receptor of compounds included in the plurality of compounds, so as to thereby identify the compound which specifically binds to the mammalian LOX-1 receptor.

In one embodiment of any of the methods described herein, the compound known to bind to the mammalian LOX-1 receptor is labeled oxidized-LDL. In one embodiment, the binding of labeled oxidized-LDL to the LOX-1 receptor is measured by quantifying the amount of labeled oxidized-LDL inside the cells. In different embodiments, oxidized-LDL is labeled with a fluorescent label, a radioactive label, or a calorimetric label. In one embodiment, oxidized-LDL is labeled with $^3$H. In one embodiment, the cells do not normally express the mammalian LOX-1 receptor and the mammalian LOX-1 receptor is encoded by any of the isolated nucleic acids described herein.

The invention provides a method involving competitive binding for identifying a chemical compound which specifically binds to a mammalian soluble LOX-1 receptor which comprises contacting the mammalian soluble LOX-1 receptor with both the chemical compound and a second chemical compound known to bind to the receptor, and separately with only the second chemical compound, under conditions suitable for binding of both compounds, and measuring specific binding of the second chemical compound to the mammalian soluble LOX-1 receptor, a decrease in the binding of the second chemical compound to the mammalian soluble LOX-1 receptor in the presence of the chemical compound indicating that the chemical compound binds to the mammalian soluble LOX-1 receptor. In one embodiment, the mammalian soluble LOX-1 receptor is immobilized on a solid surface. In one embodiment, the second chemical compound is labeled oxidized-LDL. In different embodiments, oxidized-LDL is labeled with a fluorescent label, a radioactive label, or a calorimetric label. In one embodiment, oxidized-LDL is labeled with $^3$H. In one embodiment, the mammalian soluble LOX-1 receptor is encoded by any of the isolated nucleic acids described herein.

The invention provides a method of screening a plurality of chemical compounds not known to bind to a mammalian soluble LOX-1 receptor to identify a compound which specifically binds to the mammalian soluble LOX-1 receptor, which comprises:
(a) contacting the mammalian soluble LOX-1 receptor with the plurality of compounds not known to bind specifically to the mammalian soluble LOX-1 receptor, under conditions permitting binding of compounds known to bind to the mammalian soluble LOX-1 receptor;
(b) determining whether the binding of a compound known to bind to the mammalian soluble LOX-1 receptor is reduced in the presence of the compounds within the plurality of compounds, relative to the binding of the compound in the absence of the plurality of compounds; and if so
(c) separately determining the binding to the mammalian soluble LOX-1 receptor of compounds included in the plurality of compounds, so as to thereby identify the compound which specifically binds to the mammalian soluble LOX-1 receptor.

In one embodiment of any of the methods described herein, the compound known to bind to the mammalian soluble LOX-1 receptor is labeled oxidized-LDL. In different embodiments, oxidized-LDL is labeled with a fluorescent label, a radioactive label, or a colorimetric label. In one embodiment, oxidized-LDL is labeled with $^3$H. In one embodiment, the mammalian soluble LOX-1 receptor is encoded by any of the isolated nucleic acids described herein. In one embodiment, the mammalian soluble LOX-1 receptor is immobilized on a solid surface.

The invention provides a method of identifying a compound which activates a mammalian LOX-1 receptor which comprises contacting cells expressing on their cell surface the mammalian LOX-1 receptor with the compound under conditions permitting activation of the LOX-1 receptor, and detecting activation of the LOX-1 receptor, thereby identifying the compound as a compound which activates a mammalian LOX-1 receptor. In one embodiment, the cells do not normally express the mammalian LOX-1 receptor and the mammalian LOX-1 receptor is encoded by any of the isolated nucleic acids described herein.

The invention provides a method of identifying a compound which inhibits the activity of a mammalian LOX-1 receptor which comprises contacting cells expressing on their cell surface the mammalian LOX-1 receptor with the compound under conditions permitting inhibition of the activity of the LOX-1 receptor, and detecting inhibition of the activity of the LOX-1 receptor, thereby identifying the compound as a compound which inhibits the activity of a mammalian LOX-1 receptor. In one embodiment, the cells do not normally express the mammalian LOX-1 receptor and the mammalian LOX-1 receptor is encoded by any of the isolated nucleic acids described herein.

The invention provides a method of screening a plurality of chemical compounds not known to activate a mammalian LOX-1 receptor to identify a compound which activates the mammalian LOX-1 receptor which comprises:
(a) contacting cells expressing on their cell surface the mammalian LOX-1 receptor with the plurality of compounds not known to activate the mammalian LOX-1 receptor, under conditions permitting activation of the mammalian LOX-1 receptor;

(b) determining whether the activity of the mammalian LOX-1 receptor is increased in the presence of the compounds; and if so (c) separately determining whether the activation of the mammalian LOX-1 receptor is increased by each compound included in the plurality of compounds, so as to thereby identify the compound which activates the mammalian LOX-1 receptor.

The invention provides a method of screening a plurality of chemical compounds not known to inhibit the activity of a mammalian LOX-1 receptor to identify a compound which inhibits the activity of the mammalian LOX-1 receptor, which comprises:

(a) contacting cells expressing on their cell surface the mammalian LOX-1 receptor with the plurality of compounds in the presence of a known compound which activates the mammalian LOX-1 receptor, under conditions permitting activation of the mammalian LOX-1 receptor;

(b) determining whether the activity of the mammalian LOX-1 receptor is reduced in the presence of the plurality of compounds, relative to the activity of the mammalian LOX-1 receptor in the absence of the plurality of compounds; and if so (c) separately determining the inhibition of activity of the mammalian LOX-1 receptor for each compound included in the plurality of compounds, so as to thereby identify the compound which inhibits the activity of the mammalian LOX-1 receptor.

In one embodiment of any of the methods described herein, the known compound which activates the mammalian LOX-1 receptor is oxidized-LDL.

In one embodiment of any of the methods described herein, the cells do not normally express the mammalian LOX-1 receptor and the mammalian LOX-1 receptor is encoded by any of the isolated nucleic acids described herein. In one embodiment of any of the methods described herein, prior to being transfected with a vector comprising any of the nucleic acids described herein, the cells do not express a mammalian LOX-1 receptor protein. In one embodiment of any of the methods described herein, the cells do not express the mammalian LOX-1 receptor prior to being transfected with nucleic acid encoding the mammalian LOX-1 receptor, wherein the nucleic acid comprises any of the isolated nucleic acids described herein. In one embodiment of any of the methods described herein, the cells do not express the mammalian LOX-1 receptor prior to being transfected with nucleic acid encoding the mammalian LOX-1 receptor, wherein the mammalian LOX-1 receptor comprises consecutive amino acids having the following sequence: —S, X, X, E, L, K, X, X, I, X, T, X, X, X, K, L, X, E, K, S, K, E, Q, X, E, L, X, X, X, X, X, N, L, Q, E, X, L, X, R, X, A, N, X, S— (SEQ ID NO: 39), wherein X is any amino acid.

The activity of the LOX-1 receptor can be detected in different ways. In one embodiment, activation of the LOX-1 receptor is detected by measuring increased intracellular reactive oxygen species production (Cominacini et al. 2000). In one embodiment, activation of the LOX-1 receptor is detected by measuring increased activation of the transcription factor Nuclear Factor-kappaB (NF-KB) (Cominacini et al. 2000). In one embodiment, activation of the LOX-1 receptor is detected by measuring increased monocyte chemoattractant protein-1 (MCP-1) gene expression (Li and Mehta 2000). Conversely, inhibition of the activity of the LOX-1 receptor is detected by measuring a decrease in any one of the parameters recited above.

In one embodiment of any of the methods described herein, the LOX-1 receptor is a membrane-bound LOX-1 receptor. In one embodiment of any of the methods described herein, the LOX-1 receptor is a soluble LOX-1 receptor.

In one embodiment of any of the methods described herein, the mammalian LOX-1 receptor is a human LOX-1 receptor. In one embodiment of any of the methods described herein, the mammalian LOX-1 receptor is a mouse LOX-1 receptor.

In one embodiment of any of the methods described herein, the cells are insect cells. In another embodiment, the cells are mammalian cells. In a further embodiment, the cells are nonneuronal in origin. In a further embodiment, the nonneuronal cells are COS-7 cells, 293 human embryonic kidney cells, CHO cells, NIH-3T3 cells, or LM(tk-) cells.

The invention provides a method of inhibiting LOX-1 signal transduction in a subject, which comprises administering to the subject an amount of a soluble mammalian LOX-1 receptor effective to bind LOX-1 receptor ligand and reduce availability of LOX-1 receptor ligand to bind to a membrane-bound LOX-1 receptor, thereby inhibiting LOX-1 signal transduction in the subject.

The invention provides a method of inhibiting the activity of a mammalian LOX-1 receptor, which comprises contacting the receptor with an agent that inhibits the activity of a mammalian LOX-1 receptor. In one embodiment, the LOX-1 receptor is membrane-bound.

The invention provides a method of reducing the amount of a mammalian LOX-1 receptor on the surface of a cell, which comprises delivering to the cell an agent that reduces the expression of mammalian LOX-1 receptor therein. In different embodiments, the agent is a catalytic nucleic acid or an antisense nucleic acid. In one embodiment, the agent is a ribozyme.

The invention provides a method of inhibiting the ability of an agent to bind to and activate a membrane-bound mammalian LOX-1 receptor, which comprises contacting the agent with a soluble mammalian LOX-1 receptor.

The invention provides a method of treating a mammalian subject afflicted with a disorder selected from the group consisting of atherosclerosis, heart failure and stroke, comprising administering to the subject a therapeutically effective amount of an agent that inhibits the activity of LOX-1 receptors in the subject.

The invention provides a method of inhibiting the onset in a mammalian subject of a disorder selected from the group consisting of atherosclerosis, heart failure and stroke, comprising administering to the subject a prophylactically effective amount of an agent that inhibits the activity of LOX-1 receptors in the subject.

The invention provides a method of treating a mammalian subject afflicted with a disorder selected from the group consisting of atherosclerosis, heart failure and stroke, comprising administering to the subject a therapeutically effective amount of an agent that inhibits the expression of LOX-1 receptors in the subject's cells. In different embodiments, the agent is a catalytic nucleic acid or an antisense nucleic acid. In one embodiment, the agent is a ribozyme.

The invention provides a method of inhibiting the onset in a mammalian subject of a disorder selected from the group consisting of atherosclerosis, heart failure and stroke, comprising administering to the subject a prophylactically effective amount of an agent that inhibits the expression of LOX-1 receptors in the subject's cells. In different embodiments, the agent is a catalytic nucleic acid or an antisense nucleic acid. In one embodiment, the agent is a ribozyme.

The invention provides a method of treating a mammalian subject afflicted with a disorder selected from the group consisting of atherosclerosis, heart failure and stroke, comprising administering to the subject a therapeutically effective amount of a soluble LOX-1 receptor.

The invention provides a method of inhibiting the onset in a mammalian subject of a disorder selected from the group consisting of atherosclerosis, heart failure and stroke, comprising administering to the subject a prophylactically effective amount of a soluble LOX-1 receptor.

In one embodiment of any of the methods described herein, the disorder is atherosclerosis. In one embodiment, the disorder is heart failure. In one embodiment, the disorder is stroke.

In one embodiment of any of the methods described herein, the subject is a mouse. In one embodiment, the subject is a human.

The invention provides a method of treating atherosclerosis in a subject which comprises administering to the subject an amount of a soluble mammalian LOX-1 receptor effective to treat atherosclerosis in the subject.

The invention provides a method of preventing atherosclerosis in a subject which comprises administering to the subject an amount of a soluble mammalian LOX-1 receptor effective to prevent atherosclerosis in the subject. In one embodiment, the subject is known to be susceptible to atherosclerosis.

In one embodiment of any of the methods described herein, the soluble LOX-1 receptor binds LOX-1 receptor ligand and reduces availability of LOX-1 receptor ligand to bind to a membrane-bound LOX-1 receptor.

The invention provides a method of treating atherosclerosis in a subject which comprises administering to the subject an amount of a compound effective to decrease the activity of a mammalian LOX-1 receptor and treat atherosclerosis in the subject. In one embodiment, the LOX-1 receptor is a membrane-bound Lox-1 receptor.

The invention provides a method of preventing atherosclerosis in a subject which comprises administering to the subject an amount of a compound effective to decrease the activity of a mammalian LOX-1 receptor and prevent atherosclerosis in the subject. In one embodiment, the LOX-1 receptor is a membrane-bound Lox-1 receptor. In one embodiment, the subject is known to be susceptible to atherosclerosis.

This invention provides a method of determining the susceptibility of a subject to atherosclerosis, which comprises detecting soluble LOX-1 receptor in the subject's plasma, wherein the presence of soluble LOX-1 receptor indicates an decreased susceptibility to atherosclerosis. This invention provides a method of determining the susceptibility of a subject to atherosclerosis, which comprises detecting soluble LOX-1 receptor in the subject's plasma, wherein an absence of soluble LOX-1 receptor indicates an increased susceptibility to atherosclerosis.

The invention provides a method of treating inflamation in a subject which comprises administering to the subject an amount of a soluble mammalian LOX-1 receptor effective to treat inflamation in the subject. In one embodiment, the soluble LOX-1 receptor binds LOX-1 receptor ligand and reduces availability of LOX-1 receptor ligand to bind to a membrane-bound LOX-1 receptor.

The invention provides a method of treating inflammation in a subject which comprises administering to the subject an amount of a compound effective to decrease the activity of a mammalian LOX-1 receptor and treat inflammation in the subject. In one embodiment, the LOX-1 receptor is a membrane-bound Lox-1 receptor.

The invention provides a method of treating an abnormality in a subject wherein the abnormality is alleviated by decreasing the activity of a mammalian LOX-1 receptor, which comprises administering to the subject an amount of a compound effective to decrease the activity of the LOX-1 receptor, thereby treating the abnormality. In one embodiment the LOX-1 receptor is a membrane-bound LOX-1 receptor. In one embodiment the abnormality is atherosclerosis. In one embodiment the abnormality is inflammation. In one embodiment the abnormality is heart disease. In one embodiment the abnormality is stroke.

The invention provides a method of treating an abnormality in a subject wherein the abnormality is alleviated by decreasing LOX-1 signal transduction, which comprises administering to the subject an amount of a soluble mammalian LOX-1 receptor effective to bind LOX-1 receptor ligand and reduce availability of LOX-1 receptor ligand to bind to a membrane-bound LOX-1 receptor, thereby decreasing LOX-1 signal transduction and treating the abnormality. In one embodiment the abnormality is atherosclerosis. In one embodiment the abnormality is inflammation. In one embodiment the abnormality is heart disease. In one embodiment the abnormality is stroke.

In one embodiment of any of the methods described herein, the subject is a human. In one embodiment of any of the methods described herein, the mammalian LOX-1 receptor is encoded by any of the nucleic acids described herein. In one embodiment of any of the methods described herein, the compound is identified by any of the methods described herein.

The invention provides for the use of a chemical compound identified by any of the methods described herein for the preparation of a pharmaceutical composition for treating an abnormality, wherein the abnormality is alleviated by decreasing the activity of a LOX-1 receptor. In one embodiment the LOX-1 receptor is a membrane-bound LOX-1 receptor. In one embodiment the abnormality is atherosclerosis. In one embodiment the abnormality is inflammation.

This invention provides a compound identified by any one of the methods described herein. In one embodiment, the compound is not previously known to bind to a mammalian LOX-1 receptor. In one embodiment, the compound is not previously known to activate a mammalian LOX-1 receptor. In one embodiment, the compound is not previously known to inhibit the activity of a mammalian LOX-1 receptor.

The invention provides a composition which comprises a compound identified by any of the methods described herein and a carrier. This invention provides a pharmaceutical composition comprising an amount of a chemical compound identified by any of the methods described herein and a pharmaceutically acceptable carrier. The invention provides a pharmaceutical composition comprising a compound identified by a method described herein effective to increase mammalian LOX-1 receptor activity and a pharmaceutically acceptable carrier. The invention provides a pharmaceutical composition comprising a compound identified by a method described herein effective to decrease mammalian LOX-1 receptor activity and a pharmaceutically acceptable carrier.

The invention provides a method of preparing a composition which comprises identifying a compound by any of the methods described herein and admixing a carrier.

Examples of carriers include, but are not limited to, phosphate buffered saline, physiological saline, water, and emulsions, such as oil/water emulsions.

The invention provides a method for preparing a composition which comprises admixing a carrier and a pharmaceutically effective amount of a chemical compound identified by any of the methods described herein or a novel structural and functional analog or homolog thereof.

This invention provides a method of preparing a composition which comprises identifying a compound by any of the methods described herein, recovering the compound free of any LOX-1 receptor or cellular components, and admixing the compound with a pharmaceutically acceptable carrier. This invention provides a method of preparing a composition which comprises determining whether a compound binds to a mammalian LOX-1 receptor using any of the methods described herein, recovering the compound free of any LOX-1 receptor, and admixing the compound with a pharmaceutically acceptable carrier. This invention provides a method of preparing a composition which comprises determining whether a compound activates a mammalian LOX-1 receptor using any of the methods described herein, recovering the compound free of any LOX-1 receptor, and admixing the compound with a pharmaceutically acceptable carrier. This invention provides a method of preparing a composition which comprises determining whether a compound inhibits the activity of a mammalian LOX-1 receptor using any of the methods described herein, recovering the compound free of any LOX-1 receptor, and admixing the compound with a pharmaceutically acceptable carrier.

This invention provides the use of a chemical compound identified by any of the methods described herein for the preparation of a pharmaceutical composition for treating an abnormality, wherein the abnormality is alleviated by reducing the activity of a mammalian LOX-1 receptor. In one embodiment, the mammalian LOX-1 receptor is a membrane-bound LOX-1 receptor. In one embodiment, the mammalian LOX-1 receptor is a human LOX-1 receptor. In one embodiment, the abnormality is atherosclerosis. In one embodiment, the abnormality is inflamation.

In the subject invention, a "pharmaceutically or therapeutically effective amount" is any amount of a compound or agent which, when administered to a subject suffering from a disease against which the compound or agent is effective, causes reduction, remission, or regression of the disease. A "prophylactically effective amount" is any amount of a compound or agent which, when administered to a subject, inhibits the onset in the subject of a disease or disorder against which the compound or agent is effective. Furthermore, as used herein, the phrase "pharmaceutically acceptable carrier" means any of the standard pharmaceutically acceptable carriers. Examples include, but are not limited to, phosphate buffered saline, physiological saline, water, and emulsions, such as oil/water emulsions.

This invention will be better understood from the Experimental Details which follow. However, one skilled in the art will readily appreciate that the specific methods and results discussed are merely illustrative of the invention as described more fully in the claims which follow thereafter.

Experimental Details

Materials and Methods

Mice: MOLF/Ei (MOLF) and B6.129S7-Ldlr$^{tm1Her}$ (formerly C57BL/6J-Ldlr$^{tm1Her}$; hereafter referred to as B6-Ldlr0) were purchased from The Jackson Laboratory (Bar Harbor, Me.). MOLF females were mated with B6-Ldlr0 males to produce F1 mice. Female F1s were backcrossed to B6-Ldlr0 males to produce N2 mice homozygous for the Ldlr knockout allele. N2 mice were weaned onto standard laboratory chow (PicoLab Rodent 20, #5053) at 21 days of age and switched to a Western-style diet at 8–12 weeks of age. The Western diet contained 21% wt/wt butterfat and 0.15% wt/wt cholesterol (Harlan Teklad Adjusted Calories TD 88137). Mice were bled after two weeks and three months of Western diet feeding, and sacrificed at the three-month time-point. The breeding colony was produced and maintained in a specific pathogen-free environment. All mice were given ad libitum access to food and water and maintained on a standard 12-h light-dark cycle throughout the study. All experimental protocols were approved by the Institutional Animal Care and Research Advisory Committee.

Atherosclerotic lesion measurements: Anesthetized mice were sacrificed by cervical dislocation. The hearts were perfused with 0.9% NaCl by cardiac intraventricular canalization. Then, the hearts and aortic root were dissected and fixed in 10% formalin. The aortic root was sectioned, stained with oil red O, and lesion areas were quantified as described by Plump et al. (1994).

Plasma lipoprotein and insulin measurements: Mice were bled in the middle of the light cycle following a 5–6 hour fast. Retro-orbital bleeding was performed under Forane anesthesia (Baxter, Deerfield, Ill.). Blood was collected directly into heparinized capillary tubes (Becton Dickson). Plasma was separated from cells by centrifugation and stored at $-70°$ C. Isolation of HDL cholesterol by chemical precipitation (HDL reagent, Sigma), as well as enzymatic measurements of cholesterol and triglycerides (Wako Pure Chemical Industries, Ltd.), were carried out according to the manufacturers' instructions. Non-HDL cholesterol was calculated by subtracting HDL cholesterol from total cholesterol. Insulin was measured using a commercially available ELISA kit (Crystal Chem, Inc., Chicago, Ill.).

DNA extraction and LdlrKO genotyping: DNA was extracted from tail tips by a quick alkaline lysis protocol (Truett et al. 2000). The tail tips were incubated in 50 mM NaOH for 1 hour at 95° C., vortexed and neutralized in 1 M Tris (pH 8). Cellular debris was pelleted by centrifugation and the supernatant was used for polymerase chain reaction (PCR) amplification of Ldlr alleles. Ldlr for wild type allele primers (SEQ ID NOs: 1 and 2) and Ldlr for mutant allele primers (SEQ ID NOs: 3 and 4) were used for Ldlr genotyping.

Ldlr (Wild Type Allele)

Forward, 5'-ACCCCAAGACGTGCTCCCAGGATGA-3' (SEQ ID NO: 1)

Reverse, 5'-CGCAGTGCTCCTCATCTGACTTGT-3' (SEQ ID NO: 2)

Ldlr (Mutant Allele)

Forward, 5'-AGGATCTCGTCGTGACCCATGGCGA-3' (SEQ ID NO: 3)

Reverse, 5'-GAGCGGCGATACCGTAAAGCACGAGG-3' (SEQ ID NO: 4)

Ldlr typings were confirmed by measuring plasma cholesterol levels.

DNA pooling and genome scan: DNA was quantified, in quadruplicate, by spectrophotometry. Equal amounts of DNA were pooled from 10–15 mice in the top or bottom 20% of the phenotypic ranges. Separate pools were made for males and females. The final concentration of DNA in the pools was 100–150 ng/$\mu$l, such that each individual sample was represented at a concentration of 10 ng/µl in a pool. Microsatellite markers (Dietrich et al. 1992; Love et al. 1990) were typed by PCR amplification using D4Mit127 and D6Mit110 primers purchased from Research Genetics (Huntsville, Ala.). D4Mit127 primer was used to detect linkage to Athsq1, and D6Mit110 primer was used to detect linkage to Athsq2:

D4Mit127 Primer (Used To Detect Linkage To Athsq1)

Forward, 5'-TGTGCTGATGCAGGCAC-3' (SEQ ID NO: 5)
Reverse, 5'-GAGAGGAATGCTGGTAGGCA-3' (SEQ ID NO: 6);

D6Mit110 Primer (Used To Detect Linkage To Athsq2)

Forward, 5'-GATGTCAGAATACAGATACAGCA-3' (SEQ ID NO: 7)
Reverse, 5'-GTTGCAGTGGCACCCTTTAA-3' (SEQ ID NO: 8).

PCR products were separated on 7% Long Ranger polyacrylamide (FMC BioProducts) gels and scored using a LI-COR Model 4000S automated DNA sequencer (Lincoln, Nebr.) and Gene ImagIR v3.55 software (Scanalytics, Billerica, Mass.). Parental and F1 DNA samples were run alongside the pools as controls.

Testing of candidate linkages by formal linkage analysis of the backcross panel: Markers exhibiting a biased representation of alleles in the DNA pools (significantly different than the expected Mendelian distribution of 75% B6, 25% MOLF alleles for an unlinked marker) were subsequently subject to linkage analysis using the panel of 174 individual backcross samples. In addition, flanking markers were typed to confirm positive (linkage) or negative (no linkage) results using the complete panel of individuals. For positive results, chromosomal linkage maps with multiple markers were constructed to refine the localization of the QTL, as described by Welch et al. 1996. Linkage analysis was performed using MAP MANAGER QTB28PPC as described for backcrosses (Manly and Olson 1999; Paterson et al. 1991). Due to the strong effect of sex on atherosclerosis and lipoprotein phenotypes, all analyses were performed separately for males and females. Similar results were obtained using raw or square root-transformed lesion area data. A logarithm of odds (LOD) score of 3.3 was used as the threshold for "significant" linkage (Lander and Kruglyak 1995).

Statistical analysis: ANOVA was performed using STAT-VIEW 5.0 (Abacus Concepts, Inc., Berkeley, Calif.) for Macintosh computers.

Sequencing of LOX-1: Peritoneal macrophages were isolated from C57BL/6J and MOLF/Ei mice. RNA was extracted from the macrophages and reverse-transcribed. The cDNA sequences of Olr1 (more commonly referred to as LOX-1 in the literature) were determined by polymerase chain reaction using LOX-1-specific primers followed by TA cloning (Shuman 1994) and automated sequencing. The sequences of primers used to amplify the coding region of Lox-1 were as follows:

Forward, 5'-ATG ACT TTT GAT GAC AAG ATG AAG CCT GCG-3' (SEQ ID NO: 9)
Reverse, 5'-CTT CTC ATG GTC TTC TCC AGA ATC TTT AGA-3' (SEQ ID NO: 10).

Results

The distribution of aortic fatty streak lesion areas among 174 [(MOLF×B6.Ldlr0)×B6.Ldlr0] backcross mice homozygous for the Ldlr knockout allele (Mbc-Ldlr0), and the range of values in a set of B6-Ldlr0 controls, is shown in FIG. 1. Female Mbc-Ldlr0 mice exhibited 28% larger mean lesion areas than males (mean±SD: $5.1 \pm 2.2 \times 10^5$ vs. $3.7 \pm 1.9 \times 10^5$ µm$^2$/section, respectively, P<0.0001). However, there was a broad distribution of lesion values among both female and male Mbc-Ldlr0 mice. The range of lesion areas observed for the B6-Ldlr0 controls was centered around the middle of the distribution curves for both female and male Mbc-Ldlr0 mice, suggesting the presence of both resistance and susceptibility alleles within the B6 genome.

To rule out an effect of Apoa2, previously reported to have major effects on HDL cholesterol levels and aortic lesion susceptibility in other genetic crosses (Machleder et al. 1997; Mehrabian et al. 1993), the closely-linked microsatellite marker D1Mit206 was typed in the panel of 174 Mbc-Ldlr0 mice. No linkage was detected for HDL cholesterol or atherosclerosis susceptibility. The lack of association between lesion areas and genotype at the Apoa2-linked marker suggested the presence of novel susceptibility loci segregating among the Mbc-Ldlr0 mice.

To detect candidate linkages for lesion susceptibility, a genome scan was performed using a DNA pooling strategy. The mean lesion areas in Mbc-Ldlr0 mice selected for the "low" pools were $2.3 \times 10^5$ and $1.4 \times 10^5$ µm$^2$/section for females and males, respectively. The mean lesion areas for the "high" pools were $7.0 \times 10^5$ and $6.5 \times 10^5$ µm$^2$/section for females and males, respectively. A total of 88 polymorphic markers were typed, resulting in an average marker spacing of approximately 18 centiMorgans (cM). DNA pooling can usually detect linkage within 30 cM of an allele that is preferentially represented in affected individuals (Collin et al. 1996; Taylor et al. 1994).

Two candidate loci were confirmed by linkage analysis using the complete panel of 174 backcross mice (Table 1). The loci have been designated Athsq1 (Chr 4) and Athsq2 (Chr 6), for atherosclerosis susceptibility QTL 1 and 2. Athsq1 was supported by a peak LOD score of 6.2 near D4Mit127 (approximately 77 cM distal to the centromere, as listed in the Mouse Genome Database, MGD) (FIG. 2). Linkage was detected in females only, explaining 32% of the total variance of atherosclerotic lesion areas among females. Athsq2 was supported by a peak LOD score of 6.7 near D6Mit110 (62 cM distal to the centromere, as listed in MGD) (FIG. 2). The Chr 6 locus exhibited similar linkage in females (LOD=3.5, explaining 16% of the variance) and males (LOD=3.2, explaining 14% of the variance). Female and male LOD plots were coincident, indicating that a single QTL underlies the linkage in both sexes. Confidence intervals defined by a one-unit decrease in the peak LOD score were estimated to be approximately 10 cM for both Athsq1 and Athsq2.

The QTL effects on lesion areas and common risk factors for human atherosclerosis are shown in Tables 2 and 3. In females, inheritance of two copies of the B6-derived allele (BB) of Athsq1 resulted in 40% smaller mean lesion area relative to inheritance of one copy of the B6- and one copy of the MOLF-derived alleles (MB); no effect of genotype was observed in males (Table 2). Conversely, inheritance of the BB genotype at Athsg2 resulted in 28% (females) and 33% (males) larger mean lesion area relative to inheritance of the MB genotype (Table 3). Plasma total cholesterol, HDL cholesterol and non-HDL-cholesterol levels following feeding of a Western-type diet for two weeks were tested for linkage to the atherosclerosis QTLs; no significant linkages were detected for any of the phenotypes. A small difference in mean HDL cholesterol levels was observed by ANOVA in mice grouped by genotype at Athsq1 (Table 2). However, the difference was not statistically significant after correcting for multiple testing. In addition, the atherosclerosis-resistant genotype was associated with lower HDL cholesterol levels. This is opposite to what would be expected if the mechanism for atherosclerosis susceptibility determination was through regulation of HDL cholesterol levels. No other effects of the QTLs on plasma cholesterol levels were observed. Similarly, no significant linkages were detected for triglycerides, body weight or basal metabolic index (calculated as body weight divided by the squared nose to anus length) at the atherosclerosis susceptibility QTLs.

Epidemiological studies have shown an association between hyperinsulinemia and coronary atherosclerosis (Bavenholm et al. 1995; Gaudet et al. 1998), as well as clustering of cardiovascular disease risk factors (Bonora et al. 1997; Meigs et al. 2000; Mykkanen et al. 1997). To test for an association between insulin levels and atherosclerosis susceptibility in our mouse model, we compared mean fasting insulin levels in a subset of Mbc-Ldlr0 mice grouped by genotype at the Chr 4 and Chr 6 QTLs. The mice had been fed the Western-type diet for three months. No significant associations were observed (Tables 2 and 3).

The combined effect of Athsq1 and Athsq2 was estimated by comparing mean lesion areas in mice grouped by genotype at both loci (Table 4). Mice carrying both susceptible genotypes, MB at Athsq1 and BB at Athsq2, exhibited two-fold greater lesion area than mice carrying both resistant genotypes (mean±SD: $6.6 \pm 2.0 \times 10^5$ vs. $3.2 \pm 1.8 \times 10^5$ $\mu m^2$/section, respectively). Mice carrying one susceptible and one resistant genotype exhibited intermediate lesion areas. There was no evidence of interaction between the two loci by 2-way ANOVA. These data are consistent with an additive effect of Athsq1 and Athsq2 on lesion susceptibility.

Multiple isoforms (sequence variants) of LOX-1, a gene mapped to the region overlapping Athsq2, were identified from both C57BL/6J and MOLF/Ei macrophages. Isoforms are different forms of a single gene (can relate to RNA transcripts or protein products). cDNA structures were determined by comparison with published rat (Nagase et al., 1998) and human (Sawamura et al., 1997) sequences. The major isoform found in both mouse strains, Isoform 1, exhibited similar gene structure to rat and human. The conserved structure includes a 5' signal peptide domain, transmembrane domain, leucine zipper motif, unique repetitive region, and a large lectin-like domain. Alignment of the mouse isoform sequences was performed using DIALIGN 2 (Burkhard Morgenstern, 1999). The alignment revealed that novel forms of LOX-1 lacking the transmembrane domain are expressed in MOLF/Ei macrophages but not C57BL/6J.

Sequence alignment of mouse LOX-1 coding regions are shown in FIGS. 3A–3C for the following isoforms: B6-Isoform 1 (B24), rat lox-like (SEQ ID NO: 11); MOLF-Isoform 1 (M2), rat lox-like (SEQ ID NO: 12); soluble Isoform 7 (M15) (SEQ ID NO: 13); soluble Isoform 8 (M18) (SEQ ID NO: 15); and soluble Isoform 9 (M17) (SEQ ID NO: 17). The sequences represent the complete coding region of each isoform. B-Isoform 1 is the major isoform derived from strain C57BL/6J. M-Isoform 1 is the major isoform derived from strain MOLF/Ei. Isoforms 7, 8, and 9 were derived from strain MOLF/Ei but not from strain C57BL/6J. B-Isoform 1 and M-isoform 1 contain a transmembrane domain; Isoforms 7, 8, and 9 are soluble and do not contain a transmembrane domain. B-Isoform 1 and M-isoform 1 are 100% identical. Isoforms 7, 8, and 9 are nearly identical to the major form except for the deletions.

The nucleotide and amino acid sequences for nine LOX-1 isoforms are shown in FIGS. 4–12. The amino acid sequence for isoforms 2, 5, and 6 is the same even though they have different nucleotide sequences. Isoforms 2, 5, and 6 contain only intracellular and membrane-spanning regions but lack any extracellular domains. This occurs because the missing segment, which encodes the lucine zipper in isoform 1, causes a frame shift thereby introducing a stop codon. Isoforms 3 and 4 are membrane-bound.

The alignment of the amino acid sequences of the LOX-1 repeat motifs is shown in FIG. 13. Isoforms 2, 5, and 6 are truncated proteins which do not contain repeats. Isoform 9 contains a large deletion which excludes the repeats. The repeat motifs encoded by macrophage-derived isoforms of mouse LOX-1 are aligned with a homologous region encoded by endothelial-derived human LOX-1 in FIG. 13E. A signature motif for the LOX-1 receptor (SEQ ID NO: 39) is identified from this alignment.

Figure 14:
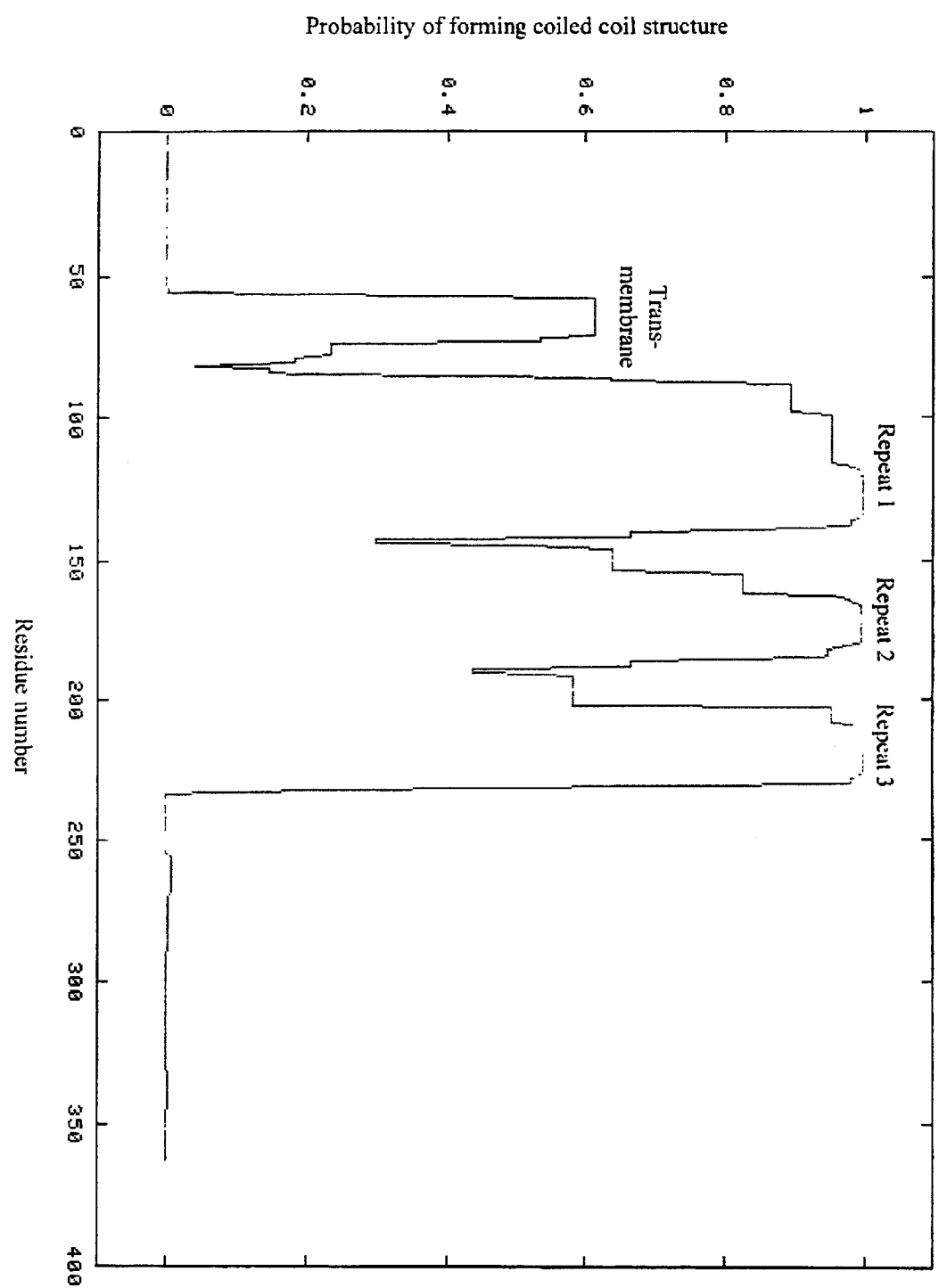
FIG. 14. Probability of regions of the LOX-1 sequence forming coiled coil structures. The repeat units of LOX-1 are predicted to form highly conserved coiled coil structures. The probability plot for Isoform 1 is shown. Figure generated using COILS software (described in Lupas et al. 1991, 1996).

The repeat units of LOX-1 are predicted to form highly conserved coiled coil structures. The probability plot for Isoform 1 is shown in FIG. 14. Since repeats 1, 2, and 3 are in the extracellular domain, they are likely to be involved in intra- or inter-molecular protein interaction which may affect the affinity of ligand binding. There is precedence for the functional importance of coiled coil structures in the extracellular domains of membrane receptors. Specifically, disruption of the coiled coil structure in the extracellular domain of macrophage scavenger receptors, which also bind and internalize modified LDL through receptor-mediated endocytosis, results in impaired endocytosis of the ligand (Doi et al. 1994).

Discussion

The Ldlr knockout model of atherosclerosis was used to map susceptibility loci to mouse Chrs 4 (Athsq1) and 6 (Athsq2). Athsq1 exhibited strong sex-specificity, contributing to disease susceptibility in females but not males. Together, genotypes at Athsq1 and Athsq2 accounted for approximately 50% of the total variance of lesion area among females. The DNA pooling strategy employed in this study allows the detection of independent susceptibility loci that are common among individuals contributing to a pool. Thus, pooling by phenotype roughly corresponds to pooling by genotype. The inability to detect QTLs contributing to the remaining 50% of the genetic variation of lesion area in this cross is likely due to genetic heterogeneity, small gene effects, and gene-gene interactions. These results are consistent with complex inheritance of atherosclerosis susceptibility in the mouse model.

In previous studies, feeding an atherogenic diet to inbred strains of mice often resulted in marked decreases of HDL cholesterol levels in atherosclerosis susceptible strains but not resistant strains (Machleder et al. 1997; Mehrabian et al. 1993; Paigen et al. 1987, 1989). This common finding led to the suggestion that genetic determinants of HDL cholesterol levels were responsible for the differences in atherosclerosis susceptibility. However, more recent studies of differential gene expression in macrophages and endothelial cells derived from resistant and susceptible strains point out that there are differences in a variety of pathways that could influence atherogenesis (Friedman et al. 2000; Shi et al. 2000).

In the current study, no significant associations were observed between Athsq1 or Athsq2 and plasma lipoprotein levels. These results suggest that in a hypercholesterolemic model of atherosclerosis, such as the Ldlr knockout model, variation in disease susceptibility is determined by factors independent of plasma lipoprotein levels. Similarly, genetic studies of atherosclerosis in the apolipoprotein E knockout model suggest a role for non-lipoprotein-related factors in determining the relative susceptibility of different mouse strains (Dansky et al. 1999; Grimsditch et al. 2000; Shi et al. 2000). The inability of cholesterol-lowering protocols to decrease risk of disease-related vents in many susceptible humans has highlighted the need to develop novel therapeutic approaches. As such, the identification of non-lipoprotein-related factors—such as those involved in inflammation, LDL oxidation, and macrophage or endothelial cell function—is an area of intense investigation in the atherosclerosis field (Glass and Wiztum 2001). Identification of the genes underlying Athsq1 and Athsq2 may shed light on novel pathways involved in atherogenesis.

Oxidized LDL is believed to be an essential component of atherogenesis that induces endothelial dysfunction and accumulation of foam cells (Ross 1993). OLR1 protein (also referred to as LOX-1) is a cell-surface receptor expressed in endothelial cells (Sawamura et al. 1997) and macrophages (Nagase et al. 1998) among other cell types; the receptor specifically binds, internalizes, and degrades oxidized LDL but not native LDL (Sawamura et al. 1997). OLR1 was shown to be expressed in atheromatous intima (Kataoka et al. 1999; Yoshida et al. 1998). Comparative sequence analysis of LOX-1, which maps to the region exhibiting peak linkage for Athsq2 (Depatie et al. 2000; Renedo et al. 2000), revealed multiple isoforms of the LOX-1 receptor in macrophages derived from the C57BL/6J and MOLF/Ei strains.

Membrane receptors lacking a transmembrane domain are soluble within the cell and may be targeted for secretion. The secretion of soluble receptors into the circulation provides a mechanism by which cells regulate signal transduction events. Thus, circulating soluble forms of a receptor bind the receptor ligand, prevent binding of the ligand to the membrane-bound receptor and inhibit downstream intracellular signalling events. The binding of oxidized low density lipoproteins to membrane-bound LOX-1 initiates a signal transduction pathway involved in the early stages of atherogenesis. Increasing the level of soluble LOX-1 receptor will increase the binding of LOX-1 ligand to the soluble receptor, thereby decreasing the binding of ligand to the LOX-1 membrane receptor, thus inhibiting LOX-1 signal transduction. This strategy may be used to prevent and treat atherogenesis.

The murine localizations of Athsq1 and Athsq2 can be used to predict the locations of human candidate susceptibility loci. Distal Chr 4 (Athsg1) and distal Chr 6 (Athsq2) exhibit extensive homologies with human Chr 1p36-32 and 12p13-12, respectively (Mouse Genome Database, The Jackson Laboratory, Bar Harbor, Me.). The regions of homology flank the confidence interval for each QTL, contain mapping data for more than 50 orthologs per region, and do not overlap any other regions of homology. Thus, Chr 1p36-32 and Chr 12p13-12 are good candidates for focused linkage analyses with densely-spaced markers. Single nucleotide polymorphisms (SNPs) covering the candidate regions have been identified (Cargill et al. 1999; Wang et al. 1998). These markers can be used in disease-association studies (Rubin and Tall 2000) to test the relevance of Athsq1 and Athsq2 in human atherosclerosis.

This application discloses novel isolated nucleic acids and their protein products which can be used in the treatment of atherosclerosis and prevention of heart attack and stroke.

TABLE 1

Linkage of lesion susceptibility QTLs to Chr 4 and Chr 6 in Mbc-Ldlr0 mice.

| Chr[1] | cM | LOD (% VAR)[2] Males (N = 92) | LOD (% VAR)[2] Females (N = 72–82) | LOD Combined (N = 174) | QTL symbol |
|---|---|---|---|---|---|
| 4 | 77 | — | 6.2 (32%) | — | Athsq1 |
| 6 | 62 | 3.2 (14%) | 3.5 (18%) | 6.7 | Athsq2 |

[1]cM, distance from the centromere in centiMorgans.
[2]LOD, logarithm of the odds ratio for linkage; % VAR, an estimate of the percent of the total variance of lesion area explained by the locus.

TABLE 2

Fatty streak lesion areas, plasma cholesterol levels, and fasting plasma insulin levels in Mbc-Ldlr0 mice grouped by genotype at D4Mit127. Values are mean ± SD.

| Genotype[1] | Lesion area ($\mu m^2$/section) | Total-C (mg/dl) | HDL-C (mg/dl) | Non-HDL-C (mg/dl) | Insulin (ng/ml) |
|---|---|---|---|---|---|
| Females | | | | | |
| BB (N = 32) | $3.6 \pm 1.8 \times 10^5$ | 344 ± 43 | 51 ± 13 | 295 ± 47 | 1.32 ± 1.0 (n = 15) |
| MB (N = 40) | $6.1 \pm 2.0 \times 10^{5*}$ | 341 ± 55 | 59 ± 16** | 284 ± 52 | 1.06 ± 0.67 (n = 7) |
| Males | | | | | |
| BB (N = 39) | $3.6 \pm 2.2 \times 10^5$ | 384 ± 57 | 71 ± 17 | 311 ± 59 | 3.16 ± 1.66 (n = 27) |
| MB (N = 48) | $3.6 \pm 2.0 \times 10^5$ | 366 ± 56 | 75 ± 15 | 291 ± 54 | 3.66 ± 2.61 (n = 10) |

[1]BB, homozygous for C57BL/6J alleles; MB, heterozygous for C57BL/6J and MOLF alleles.
*P < 0.0001 vs. BB.
**P < 0.03 vs. BB.

TABLE 3

Fatty streak lesion areas, plasma cholesterol levels, and fasting plasma insulin levels in Mbc-Ldlr0 mice grouped by genotype at D6Mit110. Values are mean ± SD.

| Genotype[1] | Lesion area ($\mu m^2$/section) | Total-C (mg/dl) | HDL-C (mg/dl) | Non-HDL-C (mg/dl) | Insulin (ng/ml) |
|---|---|---|---|---|---|
| Females | | | | | |
| BB (N = 43) | $5.8 \pm 2.0 \times 10^5$ | 342 ± 45 | 48 ± 16 | 292 ± 42 | 1.12 ± 0.79 (n = 16) |
| MB (N = 39) | $4.2 \pm 2.1 \times 10^{5*}$ | 341 ± 51 | 53 ± 14 | 286 ± 54 | 1.37 ± 1.12 (n = 7) |
| Males | | | | | |
| BB (N = 47) | $4.4 \pm 1.8 \times 10^5$ | 379 ± 50 | 66 ± 17 | 312 ± 47 | 3.42 ± 2.21 (n = 17) |
| MB (N = 45) | $2.9 \pm 1.8 \times 10^{5**}$ | 364 ± 60 | 72 ± 12 | 287 ± 61 | 3.18 ± 1.77 (n = 20) |

[1]BB, homozygous for C57BL/6J alleles; MB, heterozygous for C57BL/6J and MOLF alleles.
*$P < 0.0009$ vs. BB.
**$P < 0.0002$ vs. BB.

TABLE 4

Combined effects of Athsq1 and Athsq2 on lesion areas in 72 female Mbc-Ldlr0 mice. Values are mean ± SD in $\mu m^2$/section.

| QTL, genotype[1] | Athsq2, BB | Athsq2, BM |
|---|---|---|
| Athsq1, MB | $6.6 \pm 2.0 \times 10^5$ (N = 22) | $5.3 \pm 2.0 \times 10^5$ (N = 16) |
| Athsq1, BB | $4.1 \pm 1.4 \times 10^5$ (N = 11) | $3.2 \pm 1.8 \times 10^5$ (N = 19) |

[1]BB, homozygous for C57BL/6J alleles; MB, heterozygous for C57BL/6J and MOLF alleles.

REFERENCES

Aouizerat, B. E., Allayee, H., Cantor, R. M., Davis, R. C., Lanning, C. D., Wen, P. Z., Dallinga-Thie, G. M., de Bruin, T. W., Rotter, J. I., & Lusis, A. J. (1999) *Am. J. Hum. Genet.* 65, 397–412.

Bavenholm, P., Proudler, A., Tornvall, P., Godsland, I., Landou, C., de Faire, U., & Hamsten, A. (1995) *Circulation* 92, 1422–1429.

Bodzioch, M., Orso, E., Klucken, J., Langmann, T., Bottcher, A., Diederich, W., Drobnik, W., Barlage, S., Buchler, C., Porsch-Ozcurumez M. et al. (1999) *Nature Genet.* 22, 347–351.

Bonora, E., Targher, G., Zenere, M. B., Saggiani, F., Cacciatori, V., Tosi, F., Travia, D., Zenti, M. G., Branzi, P., Santi, L., & Muggeo, M. (1997) *Eur. J. Clin. Invest.* 27, 248–254.

Breslow, J. L. 2000. *Annu. Rev. Genet.* 34, 233–254.

Brooks-Wilson, A., Marcil, M., Clee, S. M., Zhang, L. H., Roomp, K., van Dam, M., Yu, L., Brewer, C., Collins, J. A., Moihuizen, H. O. et al. (1999) *Nature Genet.* 22, 336–345.

Burkhard Morgenstern (1999). DIALIGN 2: improvement of the segment-to-segment approach to multiple sequence alignment. Bioinformatics 15, 211–218.

Cargill, M., Altshuler, D., Ireland, J., Sklar, P., Ardlie, K., Patil, N., Shaw, N., Lane, C. R., Lim, E. P., Kalyanaraman, N. et al. (1999) *Nature Genet.* 22, 231–238.

Collin, G. B., Asada, Y., Varnum, D. S., & Nadeau, J. H. (1996) *Mamm. Genome* 7, 68–70.

Cominacini, L., Fratta Pasini, A., Garbin, U., Davoli, A., Tosetti, M. L., Campagnola, M., Rigoni, A., Pastorino, A. M., Lo Cascio, V., and Sawamura, T. (2000). Oxidized low density lipoprotein (ox-LDL) binding to ox-LDL receptor-1 in endothelial cells induces the activation of NF-KB through an increased production of intracellular reactive oxygen species. *J. Biol. Chem.* 275, 12633–12638.

Dansky, H. M., Charlton, S. A., Sikes, J. L., Heath, S. C., Simantov, R., Levin, L. F., Shu, P., Moore, K. J., Breslow, J. L., & Smith, J. D. (1999) *Arterioscler. Thromb. Vasc. Biol.* 19, 1960–1968.

Depatie, C., Lee, S-H., Stafford, A., Avner, P., Belouchi, A., Gros, P., & Vidal, S. M. (2000) *Genomics* 66, 161–174.

Dietrich, W., Katz, H., Lincoln, S. E., Shin, H. S., Friedman, J., Dracopoli, N. C., & Lander, E. S. (1992) *Genetics* 131, 423–447.

Doi, T., Kurasawa, M., Higashino, K., Imanishi, T., Mori, T., Naito, M., Takahashi, K., Kawabe, Y., Wada, Y., Matsumoto, A., et al. (1994) The histidine interruption of an alpha-helical coiled coil allosterically mediates a pH-dependent ligand dissociation from macrophage scavenger receptors. *J. Biol. Chem.* 269, 25598–25604.

Friedman, G., Ben-Yehuda, A., Dabach, Y., Hollander, G., Babaey, S., Ben-Maim, M., Stein, 0. & Stein, Y. (2000) *Arterioscler. Thromb. Vasc. Biol.* 20, 2459–2464.

Gaudet, D., Vohl, M. C., Perron, P., Tremblay, G., Gagne, C., Lesiege, D., Bergeron, J., Moorjani, S., & Despres, J. P. (1998) *Circulation* 97, 871–877.

Glass, C. K. & Wiztum, J. L. (2001) *Cell* 104, 503–516.

Grimsditch, D. C., Penfold, S., Latcham, J., Vidgeon-Hart, M., Groot, P. H., & Benson, G. M. (2000) *Atherosclerosis* 151, 389–397.

Hixson, J. E., & Blangero, J. (2000) *Ann. N.Y. Acad. Sci.* 902, 1–7.

Hobbs, H. H., Brown, M. S., & Goldstein, J. L. (1992) *Hum Mutat.* 1, 445–466.

Ishibashi, S., Brown, M. S., Goldstein, J. L., Gerard, R. D., Hammer, R. E., & Herz, J. (1993) *J. Clin. Invest.* 92, 883–893.

Kataoka, H., Kume, N., Miyamoto, S., Minami, M., Moriwaki, H., Murase, T., Sawamura, T., Masaki, T., Hashimoto, N., & Kita, T. (1999) *Circulation* 99, 3110–3117.

Keating, M. T. & Sanguinetti, M. C. (1996) *Science* 272, 681–685.

Kraus, J. P., Janosik, M., Kozich, V., Mandell, R., Shih, V., Sperandeo, M. P., Sebastio, G., de Franchis, R., Andria, G., Kluijtmans, L. A., et al. (1999) *Hum Mutat.* 13, 362–375.

Lander, E. S. & Kruglyak, L. (1995) *Nat. Genet.* 11, 241–247.

Li, D. and Mehta, J. L. (2000) Antisense to LOX-1 inhibits oxidized LDL-mediated upregulation of monocyte chemoattractant protein-1 and monocyte adhesion to human coronary artery endothelial cells. *Circulation* 101, 2889–2895.

Lifton, R. P. (1996) *Science* 272, 676–680.

Love, J. M., Knight, A. M., McAleer, M. A., & Todd, J. A. (1990) *Nucleic Acids Res.* 18, 4123–4130.

Lupas, A. (1996) Prediction and analysis of coiled-coil structures. *Meth. Enzymology* 266, 513–525.

Lupas, A., Van Dyke, M., and Stock, J. (1991) Predicting coiled coils for protein sequences. *Science* 252, 1162–1164.

Machleder, D., Ivandic, B., Welch, C., Castellani, L., Reue, K., & Lusis, A. J. (1997) *J. Clin. Invest.* 99, 1406–1419.

Manly, K. & Olson, J. M. (1999). *Mamm. Genome* 10, 327–334.

Masucci-Magoulas, L., Goldberg, I. J., Bisgaier, C. L., Serajuddin, H., Francone, O. L., Breslow, J. L., & Tall, A. R. (1997) *Science* 275, 391–394.

Mehrabian, M., Qiao, J-H., Hyman, R., Ruddle, D., Laughton, C., & Lusis, A. J. (1993) *Arterioscler. Thromb.* 13, 1–10.

Meigs, J. B., Mittleman, M. A., Nathan, D. M., Tofler, G. H., Singer, D. E., Murphy-Sheehy, P. M., Lipinska, I., D'Agostino, R. B., & Wilson, P. W. (2000) *JAMA* 283, 221–228.

Mykkanen, L., Haffner, S. M., Ronnemaa, T., Bergman, R. N., & Laakso, M. (1997) *Am. J. Epidemiol.* 146, 315–321.

Nagase, M., Abe, J., Takahashi, K., Ando, J., Hirose, S., & Fujita, T. (1998) *J. Biol. Chem.* 273, 33702–33707.

Paigen, B. (1995) *Am. J. Clin. Nutr.* 62, 458S–462S.

Paigen, B., Nesbitt, M. N., Mitchell, D., Albee, D., & LeBoeuf, R. C. (1989) *Genetics* 122, 163–168.

Paigen, B., Mitchell, D., Reue, K., Morrow, A., Lusis, A. J., & LeBoeuf, R. C. (1987) *Proc. Natl. Acad. Sci. USA* 84, 3763–3767.

Paigen B., Morrow, A., Brandon, C., Mitchell, D., & Holmes, P. (1985) *Atherosclerosis* 57, 65–73.

Paterson, A. H., Damon, S., Hewitt, J. D., Zamir, D., Pabinowitch, H. D., Lincoln, S. E., Lander, E. S., & Tanksley, S. D. (1991) *Genetics* 127, 181–197.

Plump, A. S., Scott, C. J., & Breslow, J. L. (1994) *Proc Natl Acad Sci USA* 91, 9607–9611.

Qiao, J-H., Xie, P.-Z., Fishbein, M. C., Kreuzer, J., Drake, T. A., Demer, L. L., & Lusis, A. J. (1994) *Arterioscler Thromb.* 14, 1480–1497.

Renedo, M., Arce, I., Montgomery, K., Roda-Navarro, P., Lee, E., Kucherlapati, R., & Fernandez-Ruiz, E. (2000) *Genomics* 65, 129–136.

Rice, T., Rankinen, T., Province, M. A., Chagnon, Y. C., Perusse, L., Borecki, I. B., Bouchard, C., Rao, D. C. (2000) *Circulation* 102, 1956–1963.

Risch, N. & Merikangas, K. (1996) *Science* 273, 1516–1517.

Roberts, A. & Thompson, J. S. (1977) *Prog. Biochem. Pharmacol.* 14, 298–305.

Ross, R.(1993) *Nature* 362, 801–809.

Rubin, E. M. & Tall, A. (2000) *Nature* 407, 265–269.

Rust, S., Rosier, M., Funke, H., Real, J, Amura, Z., Piette, J. C., Deleuze, J. F., Brewer, H. B., Duverger, N., Denef le, P., et al. (1999) *Nature Genet.* 22, 352–355.

Sambrook J., Fritsch E. F., and Maniatis T. Molecular Cloning. A Laboratory Manual. Cold Spring Harbor Laboratory Press, 2$^{nd}$ Edition, 1989.

Sawamura, T., Kume, N., Aoyama, T., Moriwaki, H., Hoshikawa, H., Aiba, Y., Tanaka, T., Miwa, S., Katsura, Y., Kita, T., et al. (1997) *Nature* 386, 73–77.

Shearman, A. M., Ordovas, J. M., Cupples, L. A., Schaefer, E. J., Harmon, M. D., Shao, Y., Keen, J. D., DeStefano, A. L., Joost, O., Wilson, P. W., et al. (2000) *Hum. Mol. Genet.* 9, 1315–1320.

Shi, W., Wang, N. J., Shih, D. M., Sun, V. Z., Wang, X. & Lusis, A. J. (2000) *Circ Res.* 86, 1078–1084.

Shuman, S. (1994). Novel approach to molecular cloning and polynucleotide synthesis using Vaccinia DNA topoisomerase. *J. Biol. Chem.* 269, 32678–32684.

Stewart-Phillips, J. L., Lough, J., & Skamene, E. (1989) *Clin. Invest. Med.* 12, 121–126.

Taylor, B. A., Navin, A., & Phillips, S. J. (1994) *Genomics* 21, 626–632.

Truett, G. E., Walker, J. A., Truett, A. A., Mynatt. R. L., Heeger, P., & Warman, M. (2000) *Biotechniques* 29, 52–54.

Wang, D. G., Fan, J. B., Siao, C. J., Berno, A., Young, P., Sapolsky, R., Ghandour, G., Perkins, N., Winchester, E., Spencer, J., et al. (1998) *Science* 280, 1077–1082.

Welch, C. L., Xia, Y-R., Schechter, I., Farese, R., Mehrabian, M., Mehdizadeh, S., Warden, C. H., & Lusis, A. J. (1996) *J. Lipid Res.* 37, 1406–1421.

Yoshida, H., Kondratenko, N., Green, S., Steinberg, D., Quehenberger, O. (1998) *Biochem. J.* 334, 9–13.

What is claimed is:

1. An isolated nucleic acid encoding a protein comprising the amino acid sequence set forth in SEQ ID NO:14.

2. The nucleic acid of claim 1, wherein the nucleic acid has the sequence set forth in SEQ ID NO:13.

3. The nucleic acid of claim 1, wherein the nucleic acid is DNA or RNA.

4. The nucleic acid of claim 3, wherein the DNA is cDNA.

5. A vector comprising the nucleic acid of claim 1.

6. The vector of claim 5, wherein the vector is adapted for expression of the nucleic acid in a cell and comprises regulatory elements necessary for the expression of the nucleic acid in the cell operatively linked to the nucleic acid so as to permit expression thereof.

7. An isolated cell comprising the vector of claim 5.

8. The cell of claim 7, wherein the cell is a bacterial, amphibian, yeast, fungal, insect, or mammalian cell.

9. The cell of claim 7, wherein but for the vector present therein, the cell would not express a mammalian oxidized, low-density lipoprotein (LOX-1) receptor.

* * * * *

SEQUENCE LISTING

<160> NUMBER OF SEQ ID NOS: 40

<210> SEQ ID NO 1
<211> LENGTH: 25
<212> TYPE: DNA
<213> ORGANISM: Artificial Sequence
<220> FEATURE:
<223> OTHER INFORMATION: Primer

<400> SEQUENCE: 1
accccaagac gtgctcccag gatga                25

```
<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
cgcagtgctc ctcatctgac ttgt                                           24

<210> SEQ ID NO 3
<211> LENGTH: 25
<212> TYPE: DNA
<213> ORGANISM: Artificial Sequence
<220> FEATURE:
<223> OTHER INFORMATION: Primer

<400> SEQUENCE: 3
aggatctcgt cgtgacccat ggcga                                          25

<210> SEQ ID NO 4
<211> LENGTH: 26
<212> TYPE: DNA
<213> ORGANISM: Artificial Sequence
<220> FEATURE:
<223> OTHER INFORMATION: Primer

<400> SEQUENCE: 4
gagcggcgat accgtaaagc acgagg                                         26

<210> SEQ ID NO 5
<211> LENGTH: 17
<212> TYPE: DNA
<213> ORGANISM: Artificial Sequence
<220> FEATURE:
<223> OTHER INFORMATION: Primer

<400> SEQUENCE: 5
tgtgctgatg caggcac                                                   17

<210> SEQ ID NO 6
<211> LENGTH: 20
<212> TYPE: DNA
<213> ORGANISM: Artificial Sequence
<220> FEATURE:
<223> OTHER INFORMATION: Primer

<400> SEQUENCE: 6
gagaggaatg ctggtaggca                                                20

<210> SEQ ID NO 7
<211> LENGTH: 23
<212> TYPE: DNA
<213> ORGANISM: Artificial Sequence
<220> FEATURE:
<223> OTHER INFORMATION: Primer

<400> SEQUENCE: 7
gatgtcagaa tacagataca gca                                            23

<210> SEQ ID NO 8
<211> LENGTH: 20
<212> TYPE: DNA
<213> ORGANISM: Artificial Sequence
<220> FEATURE:
```

<223> OTHER INFORMATION: Primer

<400> SEQUENCE: 8
gttgcagtgg cacccttaa          20

<210> SEQ ID NO 9
<211> LENGTH: 30
<212> TYPE: DNA
<213> ORGANISM: Artificial Sequence
<220> FEATURE:
<223> OTHER INFORMATION: Primer

<400> SEQUENCE: 9 atgactttg atgacaagat gaagcctgcg          30

<210> SEQ ID NO 10
<211> LENGTH: 30
<212> TYPE: DNA
<213> ORGANISM: Artificial Sequence
<220> FEATURE:
<223> OTHER INFORMATION: Primer

<400> SEQUENCE: 10
cttctcatgg tcttctccag aatctttaga          30

<210> SEQ ID NO 11
<211> LENGTH: 1092
<212> TYPE: DNA
<213> ORGANISM: Murinae gen. sp.
<220> FEATURE:
<221> NAME/KEY: misc_feature
<223> OTHER INFORMATION: B-Isoform 1

<400> SEQUENCE: 11

| | | | | | |
|---|---|---|---|---|---|
| atgactttg | atgacaagat | gaagcctgcg | aatgacgagc | ctgatcagaa | gtcatgtggc | 60 |
| aagaagccta | aaggtctgca | tttgctttct | tccccatggt | ggttccctgc | tgctatgact | 120 |
| ctggtcatcc | tctgcctggt | gttgtcagtg | acccttattg | tacagtggac | acaattacgc | 180 |
| caggtatctg | acctcttaaa | acaataccaa | gcgaaccta | ctcagcagga | tcgtatcctg | 240 |
| gaagggcaga | tgttagccca | gcagaaggca | gaaaacactt | cacaggaatc | aaagaaggaa | 300 |
| ctgaaaggaa | agatagacac | cctcacccag | aagctgaacg | agaaatccaa | agagcaggag | 360 |
| gagcttctac | agaagaatca | gaacctccaa | gaagccctgc | aaagagctgc | aaactcttca | 420 |
| gaggagtccc | agagagaact | caagggaaag | atagacacca | tcacccggaa | gctggacgag | 480 |
| aaatccaaag | agcaggagga | gcttctgcag | atgattcaga | acctccaaga | agccctgcag | 540 |
| agagctgcaa | actcttcaga | ggagtccag | agagaactca | agggaaagat | agacaccctc | 600 |
| accttgaagc | tgaacgagaa | atccaaagag | caggaggagc | ttctacagaa | gaatcagaac | 660 |
| ctccaagaag | ccctgcaaag | agctgcaaac | ttttcaggtc | cttgtccaca | agactggctc | 720 |
| tggcataaag | aaaactgtta | cctcttccat | gggccccta | gctgggaaaa | aaaccggcag | 780 |
| acctgccaat | ctttgggtgg | ccagttacta | caaattaatg | gtgcagatga | tctgacattc | 840 |
| atcttacaag | caatttccca | taccacctcc | ccgttctgga | ttggattgca | tcggaagaag | 900 |
| cctggccaac | catggctatg | ggagaatgga | actccttga | attttcaatt | ctttaagacc | 960 |
| aggggcgttt | ctttacagct | actccttga | attttcaatt | ctttaagacc | aggggcgttt | 1020 |
| ctttacagct | aaaactgcat | tctaattgca | ttcagcatat | gtcagaagaa | gacaaatcat | 1080 |
| ttgcaaattt | ag | | | | | 1092 |

-continued

```
<210> SEQ ID NO 12
<211> LENGTH: 1192
<212> TYPE: DNA
<213> ORGANISM: Murinae gen. sp.
<220> FEATURE:
<221> NAME/KEY: misc_feature
<223> OTHER INFORMATION: M-Isoform 1

<400> SEQUENCE: 12 atgactttg atgacaagat gaagcctgcg aatgacgagc ctgatcagaa gtcatgtggc    60
aagaagccta aggtctgca tttgctttct tccccatggt ggttccctgc tgctatgact   120
ctggtcatcc tctgcctggt gttgtcagtg acccttattg tacagtggac acaattacgc   180
caggtatctg acctcttaaa acaataccaa gcgaaccta ctcagcagga tcgtatcctg    240
gaagggcaga tgttagccca gcagaaggca gaaaacactt cacaggaatc aaagaaggaa   300
ctgaaaggaa agatagacac cctcacccag aagctgaacg agaaatccaa agagcaggag   360
gagcttctac agaagaatca agctgaacg agaaatccaa agagcaggag gagcttctac    420
agaagaatca gaacctccaa gaagccctgc aaagagctgc aaactcttca gaggagtccc   480
gaacctccaa gaagccctgc aaagagctgc aaactcttca gaggagtccc agagagaact   540
caagggaaag atagacacca tcacccggaa gctggacgag aaatccaaag agcaggagga   600
gcttctgcag atgattcaga acctccaaga agccctgcag agagctgcaa actcttcaga   660
ggagtcccag agagaactca agggaaagat agacaccctc accttgaagc tgaacgagaa   720
atccaaagag caggaggagc ttctacagaa gaatcagaac ctccaagaag ccctgcaaag   780
agctgcaaac ttttcaggtc cttgtccaca agactggctc tggcataaag aaaactgtta   840
cctcttccat gggcccttta gctggggaaaa aaaccggcag acctgccaat ctttgggtgg   900
ccagttacta caaattaatg gtgcagatga tctgacattc atcttacaag caatttccca   960
taccacctcc ccattctgga ttggattgca tcggaagaag cctggccaac catggctatg  1020
ggagaatgga actcctttga atttccaatt ctttaagacc agggcgtttt ctttacagct  1080
atattcatca ggcaactgtg catacctcca agacggagtc gtgttcgctg aaaactgcat  1140
tctaattgca ttcagcatat gtcagaagaa gacaaatcat ttgcaaattt ag         1192

<210> SEQ ID NO 13
<211> LENGTH: 744
<212> TYPE: DNA
<213> ORGANISM: Murinae gen. sp.
<220> FEATURE:
<221> NAME/KEY: CDS
<222> LOCATION: (1)..(744)
<223> OTHER INFORMATION:
<221> NAME/KEY: misc_feature
<223> OTHER INFORMATION: Isoform 7

<400> SEQUENCE: 13 atg act ttt gat gac aag atg aag cct gcg aat gac gag cct gat cag    48
Met Thr Phe Asp Asp Lys Met Lys Pro Ala Asn Asp Glu Pro Asp Gln
 1               5                  10                  15 aag tca tgt ggc aag aag cct aaa gag gag tcc cag aga gaa ctc aag    96
Lys Ser Cys Gly Lys Lys Pro Lys Glu Glu Ser Gln Arg Glu Leu Lys
             20                  25                  30 gga aag ata gac acc atc acc cgg aag ctg gac gag aaa tcc aaa gag   144
Gly Lys Ile Asp Thr Ile Thr Arg Lys Leu Asp Glu Lys Ser Lys Glu
         35                  40                  45 cag gag gag ctt ctg cag atg att cag aac ctc caa gaa gcc ctg cag   192
Gln Glu Glu Leu Leu Gln Met Ile Gln Asn Leu Gln Glu Ala Leu Gln
```

```
            50                  55                  60
aga gct gca aac tct tca gag gag tcc cag aga gaa ctc aag gga aag      240
Arg Ala Ala Asn Ser Ser Glu Glu Ser Gln Arg Glu Leu Lys Gly Lys
 65                  70                  75                  80 ata gac acc ctc acc ttg aag ctg aac gag aaa tcc aaa gag cag gag      288
Ile Asp Thr Leu Thr Leu Lys Leu Asn Glu Lys Ser Lys Glu Gln Glu
                     85                  90                  95 gag ctt cta cag aag aat cag aac ctc caa gaa gcc ctg caa aga gct      336
Glu Leu Leu Gln Lys Asn Gln Asn Leu Gln Glu Ala Leu Gln Arg Ala
                100                 105                 110 gca aac ttt tca ggt cct tgt cca caa gac tgg ctc tgg cat aaa gaa      384
Ala Asn Phe Ser Gly Pro Cys Pro Gln Asp Trp Leu Trp His Lys Glu
            115                 120                 125 aac tgt tac ctc ttc cat ggg ccc ttt ggc tgg gaa aaa aac cgg cag      432
Asn Cys Tyr Leu Phe His Gly Pro Phe Gly Trp Glu Lys Asn Arg Gln
        130                 135                 140 acc tgc caa tct ttg ggt ggc cag tta cta caa att aat ggt gca gat      480
Thr Cys Gln Ser Leu Gly Gly Gln Leu Leu Gln Ile Asn Gly Ala Asp
145                 150                 155                 160 gat ctg aca ttc atc tta caa gca att tcc cat acc acc tcc cca ttc      528
Asp Leu Thr Phe Ile Leu Gln Ala Ile Ser His Thr Thr Ser Pro Phe
                165                 170                 175 tgg att gga ttg cat cgg aag aag cct ggc caa cca tgg cta tgg gag      576
Trp Ile Gly Leu His Arg Lys Lys Pro Gly Gln Pro Trp Leu Trp Glu
            180                 185                 190 aat gga act cct ttg aat ttt caa ttc ttt aag acc agg ggc gtt tct      624
Asn Gly Thr Pro Leu Asn Phe Gln Phe Phe Lys Thr Arg Gly Val Ser
        195                 200                 205 tta cag cta tat tca tca agc aac tgt gca tac ctt caa gac gga gct      672
Leu Gln Leu Tyr Ser Ser Ser Asn Cys Ala Tyr Leu Gln Asp Gly Ala
210                 215                 220 gtg ttc gct gaa aac tgc att cta att gca ttc agc ata tgt cag aag      720
Val Phe Ala Glu Asn Cys Ile Leu Ile Ala Phe Ser Ile Cys Gln Lys
225                 230                 235                 240 aag aca aat cat ttg caa att tag                                      744
Lys Thr Asn His Leu Gln Ile
                245
```

<210> SEQ ID NO 14
<211> LENGTH: 247
<212> TYPE: PRT
<213> ORGANISM: Murinae gen. sp.
<220> FEATURE:
<221> NAME/KEY: misc_feature
<223> OTHER INFORMATION: Isoform 7

<400> SEQUENCE: 14

```
Met Thr Phe Asp Asp Lys Met Lys Pro Ala Asn Asp Glu Pro Asp Gln
 1               5                  10                  15

Lys Ser Cys Gly Lys Lys Pro Lys Glu Glu Ser Gln Arg Glu Leu Lys
                20                  25                  30

Gly Lys Ile Asp Thr Ile Thr Arg Lys Leu Asp Glu Lys Ser Lys Glu
            35                  40                  45

Gln Glu Glu Leu Leu Gln Met Ile Gln Asn Leu Gln Glu Ala Leu Gln
        50                  55                  60

Arg Ala Ala Asn Ser Ser Glu Glu Ser Gln Arg Glu Leu Lys Gly Lys
65                  70                  75                  80

Ile Asp Thr Leu Thr Leu Lys Leu Asn Glu Lys Ser Lys Glu Gln Glu
                85                  90                  95
```

-continued

```
Glu Leu Leu Gln Lys Asn Gln Asn Leu Gln Glu Ala Leu Gln Arg Ala
             100                 105                 110

Ala Asn Phe Ser Gly Pro Cys Pro Gln Asp Trp Leu Trp His Lys Glu
         115                 120                 125

Asn Cys Tyr Leu Phe His Gly Pro Phe Gly Trp Glu Lys Asn Arg Gln
     130                 135                 140

Thr Cys Gln Ser Leu Gly Gly Gln Leu Gln Ile Asn Gly Ala Asp
145                 150                 155                 160

Asp Leu Thr Phe Ile Leu Gln Ala Ile Ser His Thr Ser Pro Phe
                 165                 170                 175

Trp Ile Gly Leu His Arg Lys Lys Pro Gly Gln Pro Trp Leu Trp Glu
             180                 185                 190

Asn Gly Thr Pro Leu Asn Phe Gln Phe Phe Lys Thr Arg Gly Val Ser
         195                 200                 205

Leu Gln Leu Tyr Ser Ser Ser Asn Cys Ala Tyr Leu Gln Asp Gly Ala
     210                 215                 220

Val Phe Ala Glu Asn Cys Ile Leu Ile Ala Phe Ser Ile Cys Gln Lys
225                 230                 235                 240

Lys Thr Asn His Leu Gln Ile
                 245
```

<210> SEQ ID NO 15
<211> LENGTH: 606
<212> TYPE: DNA
<213> ORGANISM: Murinae gen. sp.
<220> FEATURE:
<221> NAME/KEY: CDS
<222> LOCATION: (1)..(606)
<223> OTHER INFORMATION:
<221> NAME/KEY: misc_feature
<223> OTHER INFORMATION: Isoform 8

<400> SEQUENCE: 15

```
atg act ttt gat gac aag atg aag cct gcg aat gac gag cct gat cag       48
Met Thr Phe Asp Asp Lys Met Lys Pro Ala Asn Asp Glu Pro Asp Gln
1               5                   10                  15 aag tca tgt ggc aag aag cct aaa gag gag tcc cag aga gaa ctc aag       96
Lys Ser Cys Gly Lys Lys Pro Lys Glu Glu Ser Gln Arg Glu Leu Lys
                20                  25                  30 gga aag ata gac acc ctc acc ttg aag ctg aac gag aaa tcc aaa gag      144
Gly Lys Ile Asp Thr Leu Thr Leu Lys Leu Asn Glu Lys Ser Lys Glu
            35                  40                  45 cag gag gag ctt cta cag aag aat cag aac ctc caa gaa gcc ctg caa      192
Gln Glu Glu Leu Leu Gln Lys Asn Gln Asn Leu Gln Glu Ala Leu Gln
        50                  55                  60 aga gct gca aac ttt tca ggt cct tgt cca caa gac tgg ctt tgg cat      240
Arg Ala Ala Asn Phe Ser Gly Pro Cys Pro Gln Asp Trp Leu Trp His
65                  70                  75                  80 aaa gaa aac tgt tac ctc ttc cat ggg ccc ttt agc tgg gaa aaa aac      288
Lys Glu Asn Cys Tyr Leu Phe His Gly Pro Phe Ser Trp Glu Lys Asn
                85                  90                  95 cgg cag acc tgc caa tct ttg ggt ggc cag tta cta caa att aat ggt      336
Arg Gln Thr Cys Gln Ser Leu Gly Gly Gln Leu Leu Gln Ile Asn Gly
            100                 105                 110 gca gat gat ctg aca ttc atc tta caa gca att tcc cat acc acc tcc      384
Ala Asp Asp Leu Thr Phe Ile Leu Gln Ala Ile Ser His Thr Thr Ser
        115                 120                 125 cca ttc tgg att gga ttg cat cgg aag aag cct ggc caa cca tgg cta      432
Pro Phe Trp Ile Gly Leu His Arg Lys Lys Pro Gly Gln Pro Trp Leu
    130                 135                 140
```

```
tgg gag aat gga act cct ttg aat ttt caa ttc ttt aag acc agg ggc      480
Trp Glu Asn Gly Thr Pro Leu Asn Phe Gln Phe Phe Lys Thr Arg Gly
145                 150                 155                 160 gtt tct tta cag cta tat tca tca ggc aac tgt gca tac ctt caa gac      528
Val Ser Leu Gln Leu Tyr Ser Ser Gly Asn Cys Ala Tyr Leu Gln Asp
                165                 170                 175 gga gct gtg ttc gct gaa aac tgc att cta att gca ttc agc ata tgt      576
Gly Ala Val Phe Ala Glu Asn Cys Ile Leu Ile Ala Phe Ser Ile Cys
            180                 185                 190 cag aag aag aca aat cat ttg caa att tag                              606
Gln Lys Lys Thr Asn His Leu Gln Ile
        195                 200

<210> SEQ ID NO 16
<211> LENGTH: 201
<212> TYPE: PRT
<213> ORGANISM: Murinae gen. sp.
<220> FEATURE:
<221> NAME/KEY: misc_feature
<223> OTHER INFORMATION: Isoform 8

<400> SEQUENCE: 16

Met Thr Phe Asp Asp Lys Met Lys Pro Ala Asn Asp Glu Pro Asp Gln
1               5                   10                  15

Lys Ser Cys Gly Lys Lys Pro Lys Glu Glu Ser Gln Arg Glu Leu Lys
            20                  25                  30

Gly Lys Ile Asp Thr Leu Thr Leu Lys Leu Asn Glu Lys Ser Lys Glu
        35                  40                  45

Gln Glu Glu Leu Leu Gln Lys Asn Gln Asn Leu Gln Glu Ala Leu Gln
    50                  55                  60

Arg Ala Ala Asn Phe Ser Gly Pro Cys Pro Gln Asp Trp Leu Trp His
65                  70                  75                  80

Lys Glu Asn Cys Tyr Leu Phe His Gly Pro Phe Ser Trp Glu Lys Asn
                85                  90                  95

Arg Gln Thr Cys Gln Ser Leu Gly Gly Gln Leu Leu Gln Ile Asn Gly
            100                 105                 110

Ala Asp Asp Leu Thr Phe Ile Leu Gln Ala Ile Ser His Thr Thr Ser
        115                 120                 125

Pro Phe Trp Ile Gly Leu His Arg Lys Lys Pro Gly Gln Pro Trp Leu
    130                 135                 140

Trp Glu Asn Gly Thr Pro Leu Asn Phe Gln Phe Phe Lys Thr Arg Gly
145                 150                 155                 160

Val Ser Leu Gln Leu Tyr Ser Ser Gly Asn Cys Ala Tyr Leu Gln Asp
                165                 170                 175

Gly Ala Val Phe Ala Glu Asn Cys Ile Leu Ile Ala Phe Ser Ile Cys
            180                 185                 190

Gln Lys Lys Thr Asn His Leu Gln Ile
        195                 200

<210> SEQ ID NO 17
<211> LENGTH: 468
<212> TYPE: DNA
<213> ORGANISM: Murinae gen. sp.
<220> FEATURE:
<221> NAME/KEY: CDS
<222> LOCATION: (1)..(468)
<223> OTHER INFORMATION:
<221> NAME/KEY: misc_feature
<223> OTHER INFORMATION: Isoform 9
```

```
<400> SEQUENCE: 17 atg act ttt gat gac aag atg aag cct gcg aat gac gag cct gat cag      48
Met Thr Phe Asp Asp Lys Met Lys Pro Ala Asn Asp Glu Pro Asp Gln
1               5                   10                  15 aag tca tgt ggc aag aag cct aaa ggt cct tgt cca caa gac tgg ctc      96
Lys Ser Cys Gly Lys Lys Pro Lys Gly Pro Cys Pro Gln Asp Trp Leu
                20                  25                  30 tgg cat aaa gaa aac tgt tac ctc ttc cat ggg ccc ttt agc tgg gaa     144
Trp His Lys Glu Asn Cys Tyr Leu Phe His Gly Pro Phe Ser Trp Glu
            35                  40                  45 aaa aac cgg cag acc tgc caa tct ttg ggt ggc cag tta cta caa att     192
Lys Asn Arg Gln Thr Cys Gln Ser Leu Gly Gly Gln Leu Leu Gln Ile
        50                  55                  60 aat ggt gca gat gat ctg aca ttc atc tta caa gca att tcc cat acc     240
Asn Gly Ala Asp Asp Leu Thr Phe Ile Leu Gln Ala Ile Ser His Thr
65                  70                  75                  80 acc tcc cca ttc tgg att gga ttg cat cgg aag aag cct ggc caa cca     288
Thr Ser Pro Phe Trp Ile Gly Leu His Arg Lys Lys Pro Gly Gln Pro
                85                  90                  95 tgg cta tgg gag aat gga act cct ttg aat ttt caa ttc ttt aag acc     336
Trp Leu Trp Glu Asn Gly Thr Pro Leu Asn Phe Gln Phe Phe Lys Thr
            100                 105                 110 agg ggc gtt tct tta cag cta tat tca tca ggc aac tgt gca tac ctt     384
Arg Gly Val Ser Leu Gln Leu Tyr Ser Ser Gly Asn Cys Ala Tyr Leu
        115                 120                 125 caa gac gga gct gtg ttc gct gaa aac tgc att cta att gca ttc agc     432
Gln Asp Gly Ala Val Phe Ala Glu Asn Cys Ile Leu Ile Ala Phe Ser
130                 135                 140 ata tgt cag aag aag aca aat cat ttg caa att tag                     468
Ile Cys Gln Lys Lys Thr Asn His Leu Gln Ile
145                 150                 155

<210> SEQ ID NO 18
<211> LENGTH: 155
<212> TYPE: PRT
<213> ORGANISM: Murinae gen. sp.
<220> FEATURE:
<221> NAME/KEY: misc_feature
<223> OTHER INFORMATION: Isoform 9

<400> SEQUENCE: 18

Met Thr Phe Asp Asp Lys Met Lys Pro Ala Asn Asp Glu Pro Asp Gln
1               5                   10                  15

Lys Ser Cys Gly Lys Lys Pro Lys Gly Pro Cys Pro Gln Asp Trp Leu
                20                  25                  30

Trp His Lys Glu Asn Cys Tyr Leu Phe His Gly Pro Phe Ser Trp Glu
            35                  40                  45

Lys Asn Arg Gln Thr Cys Gln Ser Leu Gly Gly Gln Leu Leu Gln Ile
        50                  55                  60

Asn Gly Ala Asp Asp Leu Thr Phe Ile Leu Gln Ala Ile Ser His Thr
65                  70                  75                  80

Thr Ser Pro Phe Trp Ile Gly Leu His Arg Lys Lys Pro Gly Gln Pro
                85                  90                  95

Trp Leu Trp Glu Asn Gly Thr Pro Leu Asn Phe Gln Phe Phe Lys Thr
            100                 105                 110

Arg Gly Val Ser Leu Gln Leu Tyr Ser Ser Gly Asn Cys Ala Tyr Leu
        115                 120                 125

Gln Asp Gly Ala Val Phe Ala Glu Asn Cys Ile Leu Ile Ala Phe Ser
130                 135                 140
```

```
Ile Cys Gln Lys Lys Thr Asn His Leu Gln Ile
145                 150                 155

<210> SEQ ID NO 19
<211> LENGTH: 1092
<212> TYPE: DNA
<213> ORGANISM: Murinae gen. sp.
<220> FEATURE:
<221> NAME/KEY: CDS
<222> LOCATION: (1)..(1092)
<223> OTHER INFORMATION:
<221> NAME/KEY: misc_feature
<223> OTHER INFORMATION: Isoform 1

<400> SEQUENCE: 19 atg act ttt gat gac aag atg aag cct gcg aat gac gag cct gat cag       48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca       96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg      144
Trp Trp Phe Pro Ala Ala Met Thr Leu Val Ile Leu Cys Leu Val Leu
        35                  40                  45 tca gtg acc ctt att gta cag tgg aca caa tta cgc cag gta tct gac      192
Ser Val Thr Leu Ile Val Gln Trp Thr Gln Leu Arg Gln Val Ser Asp
    50                  55                  60 ctc tta aaa caa tac caa gcg aac ctt act cag cag gat cgt atc ctg      240
Leu Leu Lys Gln Tyr Gln Ala Asn Leu Thr Gln Gln Asp Arg Ile Leu
65                  70                  75                  80 gaa ggg cag atg tta gcc cag cag aag gca gaa aac act tca cag gaa      288
Glu Gly Gln Met Leu Ala Gln Gln Lys Ala Glu Asn Thr Ser Gln Glu
                85                  90                  95 tca aag aag gaa ctg aaa gga aag ata gac acc ctc acc cag aag ctg      336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac      384
Asn Glu Lys Ser Lys Glu Gln Glu Glu Leu Leu Gln Lys Asn Gln Asn
        115                 120                 125 ctc caa gaa gcc ctg caa aga gct gca aac tct tca gag gag tcc cag      432
Leu Gln Glu Ala Leu Gln Arg Ala Ala Asn Ser Ser Glu Glu Ser Gln
    130                 135                 140 aga gaa ctc aag gga aag ata gac acc atc acc cgg aag ctg gac gag      480
Arg Glu Leu Lys Gly Lys Ile Asp Thr Ile Thr Arg Lys Leu Asp Glu
145                 150                 155                 160 aaa tcc aaa gag cag gag gag ctt ctg cag atg att cag aac ctc caa      528
Lys Ser Lys Glu Gln Glu Glu Leu Leu Gln Met Ile Gln Asn Leu Gln
                165                 170                 175 gaa gcc ctg cag aga gct gca aac tct tca gag gag tcc cag aga gaa      576
Glu Ala Leu Gln Arg Ala Ala Asn Ser Ser Glu Glu Ser Gln Arg Glu
            180                 185                 190 ctc aag gga aag ata gac acc ctc acc ttg aag ctg aac gag aaa tcc      624
Leu Lys Gly Lys Ile Asp Thr Leu Thr Leu Lys Leu Asn Glu Lys Ser
        195                 200                 205 aaa gag cag gag gag ctt cta cag aag aat cag aac ctc caa gaa gcc      672
Lys Glu Gln Glu Glu Leu Leu Gln Lys Asn Gln Asn Leu Gln Glu Ala
    210                 215                 220 ctg caa aga gct gca aac ttt tca ggt cct tgt cca caa gac tgg ctc      720
Leu Gln Arg Ala Ala Asn Phe Ser Gly Pro Cys Pro Gln Asp Trp Leu
225                 230                 235                 240 tgg cat aaa gaa aac tgt tac ctc ttc cat ggg ccc ttt agc tgg gaa      768
```

```
Trp His Lys Glu Asn Cys Tyr Leu Phe His Gly Pro Phe Ser Trp Glu
                245                 250                 255 aaa aac cgg cag acc tgc caa tct ttg ggt ggc cag tta cta caa att      816
Lys Asn Arg Gln Thr Cys Gln Ser Leu Gly Gly Gln Leu Leu Gln Ile
            260                 265                 270 aat ggt gca gat gat ctg aca ttc atc tta caa gca att tcc cat acc      864
Asn Gly Ala Asp Asp Leu Thr Phe Ile Leu Gln Ala Ile Ser His Thr
        275                 280                 285 acc tcc cca ttc tgg att gga ttg cat cgg aag aag cct ggc caa cca      912
Thr Ser Pro Phe Trp Ile Gly Leu His Arg Lys Lys Pro Gly Gln Pro
    290                 295                 300 tgg cta tgg gag aat gga act cct ttg aat ttt caa ttc ttt aag acc      960
Trp Leu Trp Glu Asn Gly Thr Pro Leu Asn Phe Gln Phe Phe Lys Thr
305                 310                 315                 320 agg ggc gtt tct tta cag cta tat tca tca ggc aac tgt gca tac ctt     1008
Arg Gly Val Ser Leu Gln Leu Tyr Ser Ser Gly Asn Cys Ala Tyr Leu
                325                 330                 335 caa gac gga gct gtg ttc gct gaa aac tgc att cta att gca ttc agc     1056
Gln Asp Gly Ala Val Phe Ala Glu Asn Cys Ile Leu Ile Ala Phe Ser
            340                 345                 350 ata tgt cag aag aag aca aat cat ttg caa att tag                     1092
Ile Cys Gln Lys Lys Thr Asn His Leu Gln Ile
        355                 360

<210> SEQ ID NO 20
<211> LENGTH: 363
<212> TYPE: PRT
<213> ORGANISM: Murinae gen. sp.
<220> FEATURE:
<221> NAME/KEY: misc_feature
<223> OTHER INFORMATION: Isoform 1

<400> SEQUENCE: 20

Met Thr Phe Asp Asp Lys Met Lys Pro Ala Asn Asp Glu Pro Asp Gln
1               5                   10                  15

Lys Ser Cys Gly Lys Lys Pro Lys Gly Leu His Leu Leu Ser Ser Pro
            20                  25                  30

Trp Trp Phe Pro Ala Ala Met Thr Leu Val Ile Leu Cys Leu Val Leu
        35                  40                  45

Ser Val Thr Leu Ile Val Gln Trp Thr Gln Leu Arg Gln Val Ser Asp
    50                  55                  60

Leu Leu Lys Gln Tyr Gln Ala Asn Leu Thr Gln Gln Asp Arg Ile Leu
65                  70                  75                  80

Glu Gly Gln Met Leu Ala Gln Lys Ala Glu Asn Thr Ser Gln Glu
                85                  90                  95

Ser Lys Lys Glu Leu Lys Gly Lys Ile Asp Thr Leu Thr Gln Lys Leu
            100                 105                 110

Asn Glu Lys Ser Lys Glu Gln Glu Leu Leu Gln Lys Asn Gln Asn
            115                 120                 125

Leu Gln Glu Ala Leu Gln Arg Ala Ala Asn Ser Ser Glu Glu Ser Gln
        130                 135                 140

Arg Glu Leu Lys Gly Lys Ile Asp Thr Ile Thr Arg Lys Leu Asp Glu
145                 150                 155                 160

Lys Ser Lys Glu Gln Glu Glu Leu Leu Gln Met Ile Gln Asn Leu Gln
                165                 170                 175

Glu Ala Leu Gln Arg Ala Ala Asn Ser Ser Glu Glu Ser Gln Arg Glu
            180                 185                 190

Leu Lys Gly Lys Ile Asp Thr Leu Thr Leu Lys Leu Asn Glu Lys Ser
```

-continued

```
                195                 200                 205
Lys Glu Gln Glu Glu Leu Leu Gln Lys Asn Gln Asn Leu Gln Glu Ala
    210                 215                 220

Leu Gln Arg Ala Ala Asn Phe Ser Gly Pro Cys Pro Gln Asp Trp Leu
225                 230                 235                 240

Trp His Lys Glu Asn Cys Tyr Leu Phe His Gly Pro Phe Ser Trp Glu
                245                 250                 255

Lys Asn Arg Gln Thr Cys Gln Ser Leu Gly Gly Gln Leu Leu Gln Ile
            260                 265                 270

Asn Gly Ala Asp Asp Leu Thr Phe Ile Leu Gln Ala Ile Ser His Thr
        275                 280                 285

Thr Ser Pro Phe Trp Ile Gly Leu His Arg Lys Pro Gly Gln Pro
290                 295                 300

Trp Leu Trp Glu Asn Gly Thr Pro Leu Asn Phe Gln Phe Lys Thr
305                 310                 315                 320

Arg Gly Val Ser Leu Gln Leu Tyr Ser Ser Gly Asn Cys Ala Tyr Leu
                325                 330                 335

Gln Asp Gly Ala Val Phe Ala Glu Asn Cys Ile Leu Ile Ala Phe Ser
            340                 345                 350

Ile Cys Gln Lys Lys Thr Asn His Leu Gln Ile
        355                 360

<210> SEQ ID NO 21
<211> LENGTH: 773
<212> TYPE: DNA
<213> ORGANISM: Murinae gen. sp.
<220> FEATURE:
<221> NAME/KEY: CDS
<222> LOCATION: (1)..(174)
<223> OTHER INFORMATION:
<221> NAME/KEY: misc_feature
<223> OTHER INFORMATION: Isoform 2

<400> SEQUENCE: 21 atg act ttt gat gac aag atg aag cct gcg aat gac gag cct gat cag    48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca    96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg   144
Trp Trp Phe Pro Ala Ala Met Thr Leu Val Ile Leu Cys Leu Val Leu
        35                  40                  45 tca gtg acc ctt att gta cag tgg aca caa tgatcgtatc ctggaagggc     194
Ser Val Thr Leu Ile Val Gln Trp Thr Gln
    50                  55 agatgttagc ccagcagaag gcagaaaaca cttcacagga atcaaagaag gaactgaaag   254
gaaagataga cacccctcacc cagaagctga acgagaaatc caaagagcag gaggagcttc   314
tacagaagaa tcagaacctc aagaagccc tgcaaagagc tgcaaactct tcagaggagt    374
cccagagaga actcaaggga agatagaca ccatcacccg gaagctggac gagaaatcca    434 agagcagga ggagcttctg cagatgattc agaacctcca agaagccctg cagagagctg    494
caaactcttc agaggagtcc cagagagaac tcaaggaaa gatagacacc ctcaccttga    554
agctgaacga gaaatccaaa gagcaggagg agcttctaca agaatcag aacctccaag    614 aagccctgca aagagctgca aacttttcag gtccttgtcc acaagactgg ctctggcata   674
aagaaaactg ttacctcttc cgtgggccct ttactgggaa aaaagccggc agacctgcca   734
```

```
atctttgggt ggcagttact acaaattaat gggcagatg                          773
```

<210> SEQ ID NO 22
<211> LENGTH: 58
<212> TYPE: PRT
<213> ORGANISM: Murinae gen. sp.
<220> FEATURE:
<221> NAME/KEY: misc_feature
<223> OTHER INFORMATION: Isoform 2

<400> SEQUENCE: 22

```
Met Thr Phe Asp Asp Lys Met Lys Pro Ala Asn Asp Glu Pro Asp Gln
 1               5                  10                  15

Lys Ser Cys Gly Lys Lys Pro Lys Gly Leu His Leu Leu Ser Ser Pro
             20                  25                  30

Trp Trp Phe Pro Ala Ala Met Thr Leu Val Ile Leu Cys Leu Val Leu
         35                  40                  45

Ser Val Thr Leu Ile Val Gln Trp Thr Gln
     50                  55
```

<210> SEQ ID NO 23
<211> LENGTH: 495
<212> TYPE: DNA
<213> ORGANISM: Murinae gen. sp.
<220> FEATURE:
<221> NAME/KEY: CDS
<222> LOCATION: (1)..(495)
<223> OTHER INFORMATION:
<221> NAME/KEY: misc_feature
<223> OTHER INFORMATION: Isoform 3

<400> SEQUENCE: 23

```
atg act ttt gat gac aag atg aag cct gcg aat gac gag cct gat cag      48
Met Thr Phe Asp Asp Lys Met Lys Pro Ala Asn Asp Glu Pro Asp Gln
 1               5                  10                  15 aag tca tgt ggc aag aag cct aaa ggt ctg cat ttg ctt tct tcc cca      96
Lys Ser Cys Gly Lys Lys Pro Lys Gly Leu His Leu Leu Ser Ser Pro
             20                  25                  30 tgg tgg ttc cct gct gct atg act ctg gtc atc ctc tgc ctg gtg ttg     144
Trp Trp Phe Pro Ala Ala Met Thr Leu Val Ile Leu Cys Leu Val Leu
         35                  40                  45 tca gtg acc ctt att gta cag tgg aca caa tta cgc cag gta tct gac     192
Ser Val Thr Leu Ile Val Gln Trp Thr Gln Leu Arg Gln Val Ser Asp
     50                  55                  60 ctc tta aaa caa tac caa gcg aac ctt act cag cag gat cgt atc ctg     240
Leu Leu Lys Gln Tyr Gln Ala Asn Leu Thr Gln Gln Asp Arg Ile Leu
65                   70                  75                  80 gaa ggg cag atg tta gcc cag cag aag gca gaa aac act tca ccg caa     288
Glu Gly Gln Met Leu Ala Gln Gln Lys Ala Glu Asn Thr Ser Pro Gln
                 85                  90                  95 tca aag aag gaa ctg aaa gga aag ata gac acc ctc acc cag aag ctg     336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac     384
Asn Glu Lys Ser Lys Glu Gln Glu Glu Leu Leu Gln Lys Asn Gln Asn
        115                 120                 125 ctc caa gaa gcc ctg caa aga gct gca aac tct tca gag gag tcc cag     432
Leu Gln Glu Ala Leu Gln Arg Ala Ala Asn Ser Ser Glu Glu Ser Gln
    130                 135                 140 aga gaa ctc aag gga aag ata gac acc ctc acc ttg aag ctg aac gag     480
Arg Glu Leu Lys Gly Lys Ile Asp Thr Leu Thr Leu Lys Leu Asn Glu
145                 150                 155                 160
```

```
aaa tcc aaa gag cag                                              495
Lys Ser Lys Glu Gln
            165

<210> SEQ ID NO 24
<211> LENGTH: 165
<212> TYPE: PRT
<213> ORGANISM: Murinae gen. sp.
<220> FEATURE:
<221> NAME/KEY: misc_feature
<223> OTHER INFORMATION: Isoform 3

<400> SEQUENCE: 24

Met Thr Phe Asp Asp Lys Met Lys Pro Ala Asn Asp Glu Pro Asp Gln
1               5                   10                  15

Lys Ser Cys Gly Lys Lys Pro Lys Gly Leu His Leu Leu Ser Ser Pro
            20                  25                  30

Trp Trp Phe Pro Ala Ala Met Thr Leu Val Ile Leu Cys Leu Val Leu
        35                  40                  45

Ser Val Thr Leu Ile Val Gln Trp Thr Gln Leu Arg Gln Val Ser Asp
    50                  55                  60

Leu Leu Lys Gln Tyr Gln Ala Asn Leu Thr Gln Gln Asp Arg Ile Leu
65                  70                  75                  80

Glu Gly Gln Met Leu Ala Gln Gln Lys Ala Glu Asn Thr Ser Pro Gln
                85                  90                  95

Ser Lys Lys Glu Leu Lys Gly Lys Ile Asp Thr Leu Thr Gln Lys Leu
            100                 105                 110

Asn Glu Lys Ser Lys Glu Gln Glu Leu Leu Gln Lys Asn Gln Asn
        115                 120                 125

Leu Gln Glu Ala Leu Gln Arg Ala Ala Asn Ser Ser Glu Glu Ser Gln
    130                 135                 140

Arg Glu Leu Lys Gly Lys Ile Asp Thr Leu Thr Leu Lys Leu Asn Glu
145                 150                 155                 160

Lys Ser Lys Glu Gln
            165

<210> SEQ ID NO 25
<211> LENGTH: 621
<212> TYPE: DNA
<213> ORGANISM: Murinae gen. sp.
<220> FEATURE:
<221> NAME/KEY: CDS
<222> LOCATION: (1)..(621)
<223> OTHER INFORMATION:
<221> NAME/KEY: misc_feature
<223> OTHER INFORMATION: Isoform 4

<400> SEQUENCE: 25 atg act ttt gat gac aag atg aag cct gcg aat gac gag cct gat cag    48
Met Thr Phe Asp Asp Lys Met Lys Pro Ala Asn Asp Glu Pro Asp Gln
1               5                   10                  15 aag tca tgt ggc aag aag cct aaa ggt ctg cat ttg ctt tct tcc cca    96
Lys Ser Cys Gly Lys Lys Pro Lys Gly Leu His Leu Leu Ser Ser Pro
            20                  25                  30 tgg tgg ttc cct gct gct atg act ctg gtc atc ctc tgc ctg gtg ttg   144
Trp Trp Phe Pro Ala Ala Met Thr Leu Val Ile Leu Cys Leu Val Leu
        35                  40                  45 tca gtg acc ctt att gta cag tgg aca caa tta cgc cag gta tct gac   192
Ser Val Thr Leu Ile Val Gln Trp Thr Gln Leu Arg Gln Val Ser Asp
    50                  55                  60
```

```
ctc tta aaa caa tac caa gcg aac ctt act cag cag gat cgt atc ctg    240
Leu Leu Lys Gln Tyr Gln Ala Asn Leu Thr Gln Gln Asp Arg Ile Leu
 65              70                  75                  80 gaa ggg cag atg tta gcc cag cag aag gca gaa aac act tca cag gaa    288
Glu Gly Gln Met Leu Ala Gln Gln Lys Ala Glu Asn Thr Ser Gln Glu
                 85                  90                  95 tca aag aag gaa ctg aaa gga aag ata gac acc ctc acc cag aag ctg    336
Ser Lys Lys Glu Leu Lys Gly Lys Ile Asp Thr Leu Thr Gln Lys Leu
            100                 105                 110 aac gag aaa tcc aaa gag cag gag gag ctt cta cag aag aat cag aac    384
Asn Glu Lys Ser Lys Glu Gln Glu Glu Leu Leu Gln Lys Asn Gln Asn
        115                 120                 125 ctc caa gaa gcc ctg caa aga gct gca aac ttt tca ggt cct tgt cca    432
Leu Gln Glu Ala Leu Gln Arg Ala Ala Asn Phe Ser Gly Pro Cys Pro
130                 135                 140 caa gac tgg ctc tgg cat aaa gaa aac tgt tac ctc ttc cat ggg ccc    480
Gln Asp Trp Leu Trp His Lys Glu Asn Cys Tyr Leu Phe His Gly Pro
145                 150                 155                 160 ttt agc tgg gaa aaa aac cgg cag acc tgc caa tct ttg ggt ggc cag    528
Phe Ser Trp Glu Lys Asn Arg Gln Thr Cys Gln Ser Leu Gly Gly Gln
                165                 170                 175 tta cta caa att aat ggt gca gat gat ctg aca ttc atc tta caa gca    576
Leu Leu Gln Ile Asn Gly Ala Asp Asp Leu Thr Phe Ile Leu Gln Ala
            180                 185                 190 att tcc cat acc acc tcc ccg ttc tgg att gga ttg cat cgg aag        621
Ile Ser His Thr Thr Ser Pro Phe Trp Ile Gly Leu His Arg Lys
        195                 200                 205

<210> SEQ ID NO 26
<211> LENGTH: 207
<212> TYPE: PRT
<213> ORGANISM: Murinae gen. sp.
<220> FEATURE:
<221> NAME/KEY: misc_feature
<223> OTHER INFORMATION: Isoform 4

<400> SEQUENCE: 26

Met Thr Phe Asp Asp Lys Met Lys Pro Ala Asn Asp Glu Pro Asp Gln
  1               5                  10                  15

Lys Ser Cys Gly Lys Lys Pro Lys Gly Leu His Leu Leu Ser Ser Pro
             20                  25                  30

Trp Trp Phe Pro Ala Ala Met Thr Leu Val Ile Leu Cys Leu Val Leu
         35                  40                  45

Ser Val Thr Leu Ile Val Gln Trp Thr Gln Leu Arg Gln Val Ser Asp
     50                  55                  60

Leu Leu Lys Gln Tyr Gln Ala Asn Leu Thr Gln Gln Asp Arg Ile Leu
 65              70                  75                  80

Glu Gly Gln Met Leu Ala Gln Gln Lys Ala Glu Asn Thr Ser Gln Glu
                 85                  90                  95

Ser Lys Lys Glu Leu Lys Gly Lys Ile Asp Thr Leu Thr Gln Lys Leu
            100                 105                 110

Asn Glu Lys Ser Lys Glu Gln Glu Glu Leu Leu Gln Lys Asn Gln Asn
        115                 120                 125

Leu Gln Glu Ala Leu Gln Arg Ala Ala Asn Phe Ser Gly Pro Cys Pro
130                 135                 140

Gln Asp Trp Leu Trp His Lys Glu Asn Cys Tyr Leu Phe His Gly Pro
145                 150                 155                 160

Phe Ser Trp Glu Lys Asn Arg Gln Thr Cys Gln Ser Leu Gly Gly Gln
                165                 170                 175
```

Leu Leu Gln Ile Asn Gly Ala Asp Asp Leu Thr Phe Ile Leu Gln Ala
                180                 185                 190

Ile Ser His Thr Thr Ser Pro Phe Trp Ile Gly Leu His Arg Lys
        195                 200                 205

<210> SEQ ID NO 27
<211> LENGTH: 712
<212> TYPE: DNA
<213> ORGANISM: Murinae gen. sp.
<220> FEATURE:
<221> NAME/KEY: misc_feature
<223> OTHER INFORMATION: Isoform 5

<400> SEQUENCE: 27

| | | | | | |
|---|---|---|---|---|---|
| atgactttg | atgacaagat | gaagcctgcg | aatgacgagc | ctgatgagaa | gtcatgtggc | 60 |
| aagaagccta | aaggtctgca | tttgctttct | tccccatggt | ggttccctgc | tgctatgact | 120 |
| ctggtcatcc | tctgcctggt | gttgtcagtg | acccttattg | tacagtggac | acaatgatcg | 180 |
| tatcctggaa | gggcagatgt | tagcccagca | gaaggcagaa | acacttcac | aggaatcaaa | 240 |
| gaaggaactg | aaaggaaaga | tagacaccct | cacccagaag | ctgaacgact | ccaaagagca | 300 |
| ggaggagcta | cacccccccc | gaacctccaa | gaagccctgc | aaagagctgc | aaactcttca | 360 |
| ggtccttgtc | cacaagactg | gctctggcat | aaagaaaact | gttacctctt | ccatgggccc | 420 |
| tttagctggg | aaaaaaaccg | gcagacctgc | caatctttgg | gtgggcagtt | actacaaatt | 480 |
| aatggtgcag | atgatctgac | attcatctta | caagcaattt | cccataccac | ctccccttct | 540 |
| tggattggat | tgcatcggaa | gaagcctggc | aaccatgggt | atgggagaat | ggacttcttt | 600 |
| gaattttaat | ttttaagaca | gggcgttttt | acagttttc | ataaggactt | gtgatactta | 660 |
| gagggctggg | ttcgttgaaa | tgattctatt | ggttagcatg | tagaaaaaaa | tt | 712 |

<210> SEQ ID NO 28
<211> LENGTH: 721
<212> TYPE: DNA
<213> ORGANISM: Murinae gen. sp.
<220> FEATURE:
<221> NAME/KEY: misc_feature
<223> OTHER INFORMATION: Isoform 6

<400> SEQUENCE: 28

| | | | | | |
|---|---|---|---|---|---|
| atgactttg | atgacaagat | gaagcctgcg | aatgacgagc | ctgatcagaa | gtcatgtggc | 60 |
| aagaagccta | aaggtctgca | tttgctttct | tccccatggt | ggttccctgc | tgctatgact | 120 |
| ctggtcatcc | tctgcctggt | gttgtcagtg | acccttattg | tacagtggac | acaataggag | 180 |
| tcccagagag | aactcaaggg | aaagatagac | ccctcacct | tgaagctgaa | cgagaaatcc | 240 |
| aaagagcagg | aggagcttct | acagaagaat | cagaacctcc | aagaagccct | gcaaagagct | 300 |
| gcaaactttt | caggtccttg | tccacaagac | tggctctggc | ataaagaaaa | ctgttacctc | 360 |
| ttccatgggc | cctttagctg | gaaaaaaaac | cggcagacct | gccaatcttt | gggtggccag | 420 |
| ttactacaaa | ttaatggtgc | agatgatctg | acattcatct | tacaagcaat | ttcccatacc | 480 |
| acctccccgt | tctggattgg | attgcatcgg | aagaagcctg | gcaaccatg | gctatgggag | 540 |
| aatggaactc | ctttgaattt | tcaattcttt | aagaccaggg | cgtttcttt | acagctatat | 600 |
| tcatcaggca | actgtgcata | ccttcaagac | ggactgtgtt | cgctgaaaac | tgcattctaa | 660 |
| ttgcattcag | catatgtcaa | aagaagacaa | atcatttgca | aatttagtga | atctaaagaa | 720 |
| t | | | | | | 721 |

```
<210> SEQ ID NO 29
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 1 REPEAT #1

<400> SEQUENCE: 29

Glu Ser Lys Lys Glu Leu Lys Gly Lys Ile Asp Thr Leu Thr Gln Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Ser Ser Glu
        35                  40                  45

<210> SEQ ID NO 30
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 1 REPEAT #2

<400> SEQUENCE: 30

Glu Ser Gln Arg Glu Leu Lys Gly Lys Ile Asp Thr Ile Thr Arg Lys
1               5                   10                  15

Leu Asp Glu Lys Ser Lys Glu Gln Glu Leu Leu Gln Met Ile Gln
            20                  25                  30

Asn Leu Gln Glu Ala Leu Gln Arg Ala Ala Asn Ser Ser Glu
        35                  40                  45

<210> SEQ ID NO 31
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 1 REPEAT #3

<400> SEQUENCE: 31

Glu Ser Gln Arg Glu Leu Lys Gly Lys Ile Asp Thr Leu Thr Leu Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Phe Ser Gly
        35                  40                  45

<210> SEQ ID NO 32
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 3 REPEAT #1

<400> SEQUENCE: 32

Gln Ser Lys Lys Glu Leu Lys Gly Lys Ile Asp Thr Leu Thr Gln Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Ser Ser Glu
        35                  40                  45
```

<210> SEQ ID NO 33
<211> LENGTH: 24
<212> TYPE: PRT
<213> ORGANISM: Murinae gen. sp.
<220> FEATURE:
<221> NAME/KEY: MISC_FEATURE
<223> OTHER INFORMATION: ISOFORM 3 REPEAT #3 PARTIAL

<400> SEQUENCE: 33

Glu Ser Gln Arg Glu Leu Lys Gly Lys Ile Asp Thr Leu Thr Leu Lys
1               5                   10                  15

Leu Asn Glu Lys Ser Lys Glu Gln
            20

<210> SEQ ID NO 34
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 4 REPEAT #1

<400> SEQUENCE: 34

Glu Ser Lys Lys Glu Leu Lys Gly Lys Ile Asp Thr Leu Thr Gln Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Phe Ser Gly
            35                  40                  45

<210> SEQ ID NO 35
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 7 REPEAT#2

<400> SEQUENCE: 35

Glu Ser Gln Arg Glu Leu Lys Gly Lys Ile Asp Thr Ile Thr Arg Lys
1               5                   10                  15

Leu Asp Glu Lys Ser Lys Glu Gln Glu Leu Leu Gln Met Ile Gln
            20                  25                  30

Asn Leu Gln Glu Ala Leu Gln Arg Ala Ala Asn Ser Ser Glu
            35                  40                  45

<210> SEQ ID NO 36
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 7 REPEAT#3

<400> SEQUENCE: 36

Glu Ser Gln Arg Glu Leu Lys Gly Lys Ile Asp Thr Leu Thr Leu Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Phe Ser Gly
            35                  40                  45

```
<210> SEQ ID NO 37
<211> LENGTH: 46
<212> TYPE: PRT
<213> ORGANISM: Murinae gen. sp.
<220> FEATURE:
<221> NAME/KEY: MISC_FEATURE
<223> OTHER INFORMATION: ISOFORM 8 REPEAT#3

<400> SEQUENCE: 37

Glu Ser Gln Arg Glu Leu Lys Gly Lys Ile Asp Thr Leu Thr Leu Lys
1               5                   10                  15

Leu Asn Glu Lys Ser Lys Glu Gln Glu Leu Leu Gln Lys Asn Gln
            20                  25                  30

Asn Leu Gln Glu Ala Leu Gln Arg Ala Ala Asn Phe Ser Gly
        35                  40                  45

<210> SEQ ID NO 38
<211> LENGTH: 46
<212> TYPE: PRT
<213> ORGANISM: Homo sapiens

<400> SEQUENCE: 38

Glu Ser Glu Asn Glu Leu Lys Glu Met Ile Glu Thr Leu Ala Arg Lys
1               5                   10                  15

Leu Asn Glu Lys Ser Lys Glu Gln Met Glu Leu His His Gln Asn Leu
            20                  25                  30

Asn Leu Gln Glu Thr Leu Lys Arg Val Ala Asn Cys Ser Ala
        35                  40                  45

<210> SEQ ID NO 39
<211> LENGTH: 44
<212> TYPE: PRT
<213> ORGANISM: Unknown
<220> FEATURE:
<223> OTHER INFORMATION: SIGNATURE SEQUENCE
<221> NAME/KEY: MISC_FEATURE
<222> LOCATION: (2)..(43)
<223> OTHER INFORMATION: X = ANY AMINO ACID

<400> SEQUENCE: 39

Ser Xaa Xaa Glu Leu Lys Xaa Xaa Ile Xaa Thr Xaa Xaa Xaa Lys Leu
1               5                   10                  15

Xaa Glu Lys Ser Lys Glu Gln Xaa Glu Leu Xaa Xaa Xaa Xaa Asn
            20                  25                  30

Leu Gln Glu Xaa Leu Xaa Arg Xaa Ala Asn Xaa Ser
        35                  40

<210> SEQ ID NO 40
<211> LENGTH: 44
<212> TYPE: PRT
<213> ORGANISM: Unknown
<220> FEATURE:
<223> OTHER INFORMATION: SIGNATURE SEQUENCE COMMON TO MOUSE AND HUMAN
<221> NAME/KEY: MISC_FEATURE
<222> LOCATION: (2)..(2)
<223> OTHER INFORMATION: X = E, Q, OR K
<221> NAME/KEY: MISC_FEATURE
<222> LOCATION: (3)..(3)
<223> OTHER INFORMATION: X = N, R, OR K
<221> NAME/KEY: MISC_FEATURE
<222> LOCATION: (7)..(7)
<223> OTHER INFORMATION: X = E OR G
<221> NAME/KEY: MISC_FEATURE
<222> LOCATION: (8)..(8)
<223> OTHER INFORMATION: X = M OR K
<221> NAME/KEY: MISC_FEATURE
<222> LOCATION: (10)..(10)
```

```
<223> OTHER INFORMATION: X = E OR D
<221> NAME/KEY: MISC_FEATURE
<222> LOCATION: (12)..(12)
<223> OTHER INFORMATION: X = L OR I
<221> NAME/KEY: MISC_FEATURE
<222> LOCATION: (13)..(13)
<223> OTHER INFORMATION: X = A OR T
<221> NAME/KEY: MISC_FEATURE
<222> LOCATION: (14)..(14)
<223> OTHER INFORMATION: X = R, L, OR Q
<221> NAME/KEY: MISC_FEATURE
<222> LOCATION: (17)..(17)
<223> OTHER INFORMATION: X = N OR D
<221> NAME/KEY: MISC_FEATURE
<222> LOCATION: (24)..(24)
<223> OTHER INFORMATION: X = M OR E
<221> NAME/KEY: MISC_FEATURE
<222> LOCATION: (27)..(27)
<223> OTHER INFORMATION: X =  H OR L
<221> NAME/KEY: MISC_FEATURE
<222> LOCATION: (28)..(28)
<223> OTHER INFORMATION: X =  H OR Q
<221> NAME/KEY: MISC_FEATURE
<222> LOCATION: (29)..(29)
<223> OTHER INFORMATION: X =  Q, K OR M
<221> NAME/KEY: MISC_FEATURE
<222> LOCATION: (30)..(30)
<223> OTHER INFORMATION: X =  N OR I
<221> NAME/KEY: MISC_FEATURE
<222> LOCATION: (31)..(31)
<223> OTHER INFORMATION: X =  L OR Q
<221> NAME/KEY: MISC_FEATURE
<222> LOCATION: (36)..(36)
<223> OTHER INFORMATION: X =  T OR A
<221> NAME/KEY: MISC_FEATURE
<222> LOCATION: (38)..(38)
<223> OTHER INFORMATION: X =  K OR Q
<221> NAME/KEY: MISC_FEATURE
<222> LOCATION: (40)..(40)
<223> OTHER INFORMATION: X =  V OR A
<221> NAME/KEY: MISC_FEATURE
<222> LOCATION: (43)..(43)
<223> OTHER INFORMATION: X =  C,F OR S

<400> SEQUENCE: 40

Ser Xaa Xaa Glu Leu Lys Xaa Xaa Ile Xaa Thr Xaa Xaa Xaa Lys Leu
1               5                   10                  15

Xaa Glu Lys Ser Lys Glu Gln Xaa Glu Leu Xaa Xaa Xaa Xaa Xaa Asn
            20                  25                  30

Leu Gln Glu Xaa Leu Xaa Arg Xaa Ala Asn Xaa Ser
            35                  40
```